(12) United States Patent
Konno

(10) Patent No.: US 6,582,362 B2
(45) Date of Patent: Jun. 24, 2003

(54) ENDOSCOPE SYSTEM

(75) Inventor: Mitsujiro Konno, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 7 days.

(21) Appl. No.: 09/903,866

(22) Filed: Jul. 13, 2001

(65) Prior Publication Data
US 2002/0055669 A1 May 9, 2002

(30) Foreign Application Priority Data
Jul. 14, 2000 (JP) .......................... 2000-218729

(51) Int. Cl.$^7$ .............................. A61B 1/06; G02B 23/26
(52) U.S. Cl. ........................ 600/167; 600/168; 359/379; 359/380; 359/656
(58) Field of Search ................................ 600/112, 162, 600/167, 168; 348/65; 359/656–661, 368, 379, 380

(56) References Cited

U.S. PATENT DOCUMENTS

| 4,312,572 A | | 1/1982 | Yamashita et al. |
| 5,748,385 A | * | 5/1998 | Miyano ........................ 359/691 |
| 6,252,723 B1 | * | 6/2001 | Nagaoka ........................ 359/689 |

FOREIGN PATENT DOCUMENTS

| JP | 04-218012 | 8/1992 |
| JP | 08-136832 | 5/1996 |

* cited by examiner

Primary Examiner—John Mulcahy
(74) Attorney, Agent, or Firm—Pillsbury Winthrop LLP

(57) ABSTRACT

An endoscope system in which a normal observation image and a near observation image are photographed by a solid-state image sensor upon operation of a focus adjustment device for changing a focal length and a working distance satisfies:

$$WD_{Wide} > WD_{tele}$$

$$f_{wide} \geq f_{tele}$$

where $f_{wide}$ is a focal length in a normal observation mode, $WD_{wide}$ is a working distance in the normal observation mode, $f_{tele}$ is a focal length in a near observation mode, and $WD_{tele}$ is a working distance in the near observation mode. Whereby, the endoscope system is provided with a wide depth of field so as to allow even a person without considerable skills to easily manipulate the system in the magnifying observation mode, is able to improve accuracy of diagnosis information by enhancing seeming resolution of the magnified information, and is able to improve accuracy of diagnosis by facilitating discussion among a plurality of medical doctors.

19 Claims, 15 Drawing Sheets

NORMAL

NEAR

NORMAL

NEAR

NORMAL

NEAR

NORMAL

NEAR

NORMAL

NEAR

FIG.15

| CONDITION | REF. EX. | EMB. 1 | EMB. 2 | EMB. 3 | EMB. 4 | EMB. 5 | EMB. 6 | EMB. 7 |
|---|---|---|---|---|---|---|---|---|
| $WD_{wide}$ | 10.6 | 10.8 | 12.3 | 11 | 11 | 11 | 25 | 10.6 |
| $WD_{tele}$ | 1.6 | 1.08 | 2.2 | 1.2 | 1.2 | 1 | 2 | 1.3 |
| $fL_{wide}$ | 1.060 | 1.006 | 0.963 | 1.056 | 0.973 | 1.044 | 1.155 | 1.096 |
| $fL_{tele}$ | 2.168 | 0.842 | 0.886 | 1.056 | 1.012 | 0.883 | 1.074 | 0.946 |
| $FnO_{wide}$ | 7.969 | 12.294 | 5.626 | 10.410 | 9.547 | 7.833 | 8.143 | 11.000 |
| $FnO_{tele}$ | 12.604 | 12.293 | 5.620 | 12.783 | 11.723 | 7.529 | 8.232 | 11.400 |
| $fF_{wide}$ | 1.037 | 0.119 | 0.323 | 0.027 | 0.080 | 0.426 | 0.431 | 0.146 |
| $fF_{tele}$ | 0.470 | 0.180 | 0.348 | 0.027 | 0.082 | 0.342 | 0.408 | 0.146 |
| $Pexp_{wide}$ | 18.97 | -2.88 | -3.06 | -2.90 | -3.08 | -9.48 | -9.57 | -2.92 |
| $Pexp_{tele}$ | -7.12 | -2.88 | -3.06 | -3.69 | -4.11 | -4.50 | -7.61 | -2.92 |
| $N_{wide}$ | 5.64 | 7.15 | 7.15 | 5.70 | 5.44 | 6.15 | 10.20 | 5.59 |
| $\beta_{wide}$ | -0.159 | -0.129 | -0.129 | -0.184 | -0.176 | -0.159 | -0.109 | -0.193 |
| $F_{wide}$ | 44.10 | 40.40 | 40.40 | 151.00 | Inf | 43.25 | Inf | 90.70 |
| $N_{tele}$ | 1.50 | 1.84 | 1.84 | 1.06 | 1.05 | 0.86 | 1.68 | 1.09 |
| $\beta_{tele}$ | -1.099 | -0.405 | -0.405 | -0.969 | -0.893 | -0.735 | -0.515 | -0.749 |
| $F_{tele}$ | 1.71 | 2.70 | 2.70 | 1.38 | 1.40 | 1.18 | 2.44 | 1.60 |
| $\Delta$ | 0.21 | 0.86 | 0.86 | 0.32 | 0.35 | 0.32 | 0.76 | 0.50 |
| $Pexp_{wide}/fL_{wide}$ | 17.89 | -2.86 | -3.18 | -2.75 | -3.17 | -9.07 | -8.29 | -2.67 |
| $Pexp_{tele}/fL_{tele}$ | -3.28 | -3.42 | -3.45 | -3.50 | -4.06 | -5.09 | -7.09 | -3.09 |
| $\delta$ | 3 μm | 3 μm | 3 μm | 3 μm | 3 μm | 3 μm | 3 μm | 3 μm |
| COEFFICIENT | 3 | 3 | 3 | 3 | 3 | 3 | 3 | 3 |

ENDOSCOPE SYSTEM

BACKGROUND OF THE INVENTION

1) Field of the Invention

The present invention relates to an endoscope system that is provided with a photographing optical system using a solid-state image sensor.

2) Description of Related Art

In recent years, electronic endoscopes using solid-state image sensors such as compact CCDs have become popular. Since such an endoscope allows a plurality of persons to observe lesion in a body cavity via a TV monitor, examination and diagnosis can be made by a plurality of medical doctors. Also, it is greatly advantageous to patients also in that they can view their own lesion while being informed of doctor's diagnosis. Of such endoscopes, so-called "magnifying endoscope", which is used for near observation of lesion to facilitate examination of its minute structure for the purpose of determining the degree of infiltration of the minute lesion or the regional extent to be subjected to incision, has drawn particular attention most recently.

Some of optical systems for the magnifying endoscopes are disclosed, for example, in Japanese Patent Publication (KOKOKU) No. Sho 61-44283 and Japanese Patent Application Preliminary Publication (KOKAI) No. 4-218012. Each of these optical systems are three- or four-unit-type optical systems and are able to provide high magnification, while involving a problem in that the entire length of the optical system is considerably long, to cause bulkiness of the insertion section of the endoscope and thus to impose a great burden on a patient.

Also, such a magnifying endoscope of prior example has a drawback in that it has an extremely narrow depth of field and thus has poor operability.

Here, brief explanation is made of the definition of depth of field. FIG. 16 is a sectional view of an endoscope optical system taken along the optical axis. As shown in the drawing, placing a CCD at a position where an image I of an object O is formed makes it possible to obtain an in-focus image. If the object O is moved toward the endoscope to the position O', the image I is shifted to be formed at a position I'. On the other hand, if the object O is moved away from the endoscope to a position O", the image I is shifted to be formed at a position I". Where the position of the CCD is fixed, the image I' or the image I" at the position of the CCD becomes a circle of confusion with a diameter $\delta$, to cause an out-of-focus image. However, if the resolution of the CCD is greater than the diameter $\delta$ of the circle of confusion, image quality is determined by the resolution of the CCD and, accordingly, the object-position range from O' to O" seems to be in focus. This range is called "depth of field", where a distance $X_n$ from the optical system to the point O' is defined as the nearest distance in the range of the depth of field, while a distance $X_f$ from the optical system to the point O" is defined as the farthest distance in the range of the depth of field.

In this case, the following equation is true:

$$|1/X_n - 1/X_f| = 2\delta F_{no}/f_L^2 \quad (1)$$

where the effective aperture ratio (F number) is represented by $F_{no}$ and the focal length of the optical system is represented by $f_L^2$.

Here, the depth of field D is given by:

$$D = X_f - X_n \quad (2)$$

If we regard $X_n$, $X_f$ as two values of the variable X of the function $1/X = Y$, we can view a value of the operation on the left of Equation (1) in the form of a difference in Y direction between two points that lie on the curve of $1/X = Y$ shown in FIG. 17. If the value of $2\delta F_{no}/f_L^2$ is constant, a smaller value of $X_n$, or the near observation condition yields a smaller depth of field $D_1$.

To be specific, the depth of field of a magnifying endoscope in the magnifying mode is as narrow as 2 mm or 3 mm. Such a specification would require, for example, an operator to perform subtle manipulation on the order of 1 mm while the endoscope being inserted into the large intestine over 1m deep. In short, it requires a lot of skill to manipulate the endoscope (Problem 1).

Also, in the conventional magnifying endoscope system, the same image processing is performed in the normal observation mode and in the magnifying observation mode. In general, when a tissue is magnified, minute lesion in it also is observed as magnified and thus the image provided for observation would contain a large amount of low-frequency components. In contrast, since an endoscopic image in the normal observation mode shows a web pattern of fine blood vessels at a low magnification, the image provided for observation would contain a large amount of high-frequency components. Therefore, if the image processing that is optimized for the magnifying observation mode is employed in the normal observation mode, the image of the blood vessels collapses to be hardly observable (Problem 2).

Furthermore, according to the conventional magnifying endoscope, a part of the optical system located 1 m or more away is driven via a wire for switching between the normal observation mode and the magnifying observation mode. No medical doctor but the operator can know the magnification currently selected and thus there may be difference in recognition regarding the size of the lesion among them. Resultantly, it is difficult for them to make a discussion (Problem 3).

SUMMARY OF THE INVENTION

The present invention has been made in consideration of the above-mentioned problems involved in the conventional art. An object of the present invention is to provide an endoscope system which is made compact so as to impose less burden on a patient, is provided with a wide depth of field so as to allow even a person without considerable skills to easily manipulate the system in the magnifying observation mode, is able to improve accuracy of diagnosis information by enhancing seeming resolution regarding the magnified information, and is able to improve accuracy of diagnosis by facilitating discussion among a plurality of medical doctors.

In order to attain the above-mentioned object, the endoscope system according to the present invention is configured to photograph an image obtained in the normal observation mode and an image obtained in the near observation mode on a solid-state image sensor by controlling a focus adjustment means which changes the focal length and the working distance and to display the image on a display unit, wherein the following conditions are satisfied:

$$WD_{wide} > WD_{tele} \quad (3)$$

$$f_{wide} \geq f_{tele} \quad (4)$$

where $f_{wide}$ is a focal length in the normal observation mode, $WD_{wide}$ is a working distance in the normal observation mode, $f_{tele}$ is a focal length in the near observation mode, and $WD_{tele}$ is a working distance in the near observation mode.

In general, where $f_L$ is a focal length of an optical system, $f_F$ is a front-side focal length of the optical system and z is a distance from the surface of the optical system to an object, magnification β of the optical system is given by:

$$\beta = -f_L/(f_F + z) \quad (5)$$

Accordingly, for the purpose of securing as large a magnification β as possible, it is necessary to set the distance z as short as possible or to set the focal length $f_L$ as long as possible.

On the other hand, as explained above regarding Problem 1, if the distance z from the surface of the optical system to the object is set short or the focal length $f_L$ is set long, the depth of field becomes narrow, to make the system less operable. Condition (3) is specified, according to the present invention, so that the requirement for the magnification and the requirement for the depth of field are compatibly satisfied. This is a minimum necessary condition for securing a sufficiently high magnification. In performing magnifying observation, a medical doctor would spread coloring over lesion so that the lesion is viewed in high contrast. However, this treatment would attenuate light reflected back from the object, sometimes to make the visual field dim. If only Condition (3) is satisfied, this problem of dimness can be dealt with, because an illumination lens also can be located near the object, to improve brightness.

Condition (4) is specified, according to the present invention, for the purpose of securing as wide a depth of field as possible. As is known from Equation (1), depth of field increases with decreasing focal length $f_L$ in inverse proportion to the square of $f_L$. Therefore, the focal length in the magnifying observation mode is set to be small to satisfy the condition $f_{wide} \geq f_{tele}$, for the purpose of widen the depth of field and, simultaneously, the endoscope is positioned near the object to satisfy Condition (3) for the purpose of increasing magnification. In this way, simultaneous satisfaction of Condition (3) and Condition (4) can provide a magnifying endoscope that achieves high magnification and wide depth of field for convenience in use.

Also, an endoscope system according to the present invention is provided with a control device that supplies a control signal based on a signal from a solid-state image sensor to a focus adjustment means, wherein, on the basis of the control signals, control of switching between image processing modes is made in accordance with the situation of the optical system.

In general, in the near observation mode, the image contains low-frequency components because a pattern peculiar to the lesion is observed with a high magnification. Therefore, enhancing the low-frequency components facilitates determination of the pattern of the lesion and thus is preferable.

On the other hand, the endoscopic image in the normal observation mode contains high-frequency components because a web pattern of minute blood vessels is photographed with a low magnification. Therefore, in the normal observation mode, enhancing the high-frequency components facilitates determination of the web pattern of the blood vessels and thus is preferable.

Conventionally, only an operator who manipulates the endoscope is able to know which of the near observation mode and the normal observation mode is currently selected. Therefore, in order to optimize the above-mentioned two image processing modes in compliance with the selected observation mode, the operator has to judge the status himself and make switching manually, which is bothersome. In contrast, according to the present invention, since switching between the near observation mode and the normal observation mode is electrically controlled by the control device, determination of the selected mode is made on the basis of the control signal and switching is performed automatically. Whereby, two kinds of image processing modes for near observation and normal observation can be properly selected without confusion so as to improve accuracy of diagnosis information by enhancing seeming resolution regarding the magnified information.

Furthermore, an endoscope system according to the present invention is provided with a control device that supplies control signals based on signals from a solid-state image sensor to a focus adjustment means, a calculating device which calculates, on the basis of the control signals, optical amounts corresponding to the status of the optical system, and a display unit which displays a result of the calculation generated by the calculating device.

As described above, the optical system of the endoscope is designed to have a relatively wide depth of field. To be specific, it has an observation range varying from 5 mm wide to 100 mm wide. On the other hand, as expressed by Equation (5), the magnification of the optical system is the function of the distance z to the object and the focal length $f_L$, and thus the optical magnification associated with the depth of field 5 mm and the optical magnification associated with the depth of field 100 mm greatly differ.

Ideally, it is desirable that the dimensions of lesion are definitely determined. However, unless the distance to the lesion is known, the optical magnification cannot be determined. In this case, measurement methods typically including triangulation are not preferred because application of such a method would result in bulkiness of the endoscope distal end section.

Detailed analysis of requirements of medical doctors' has revealed that, besides accurate dimensions of lesion, common recognition among the medical doctors regarding magnification range of the object image currently in focus would remove misunderstandings in discussion among them and thus can improve accuracy of diagnosis.

According to the present invention, switching between the near observation mode and the normal observation mode is electrically controlled by the control device, where optical information peculiar to each of the near observation mode and the normal observation mode is calculated on the basis of the control signals so as to be displayed on the display unit as useful information. Whereby, since which of the near mode and the normal mode is the current observation mode and optical amounts, which typically include the magnification, in the current mode are available on the display, it is possible to provide an endoscope system which would preclude possible misunderstandings among the medical doctors and thus would improve accuracy of diagnosis.

This and other objects as well as features and advantages of the present invention will become apparent from the following detailed description of the preferred embodiments when taken in conjunction with the accompanying drawings.

BRIEF DESCRIPTION OF THE DRAWINGS

FIG. 1A shows the status in the normal observation mode and FIG. 1B shows the status in the near observation mode.

FIG. 2A shows the status in the normal observation mode and FIG. 2B shows the status in the near observation mode.

FIG. 4A shows the status in the normal observation mode and FIG. 4B shows the status in the near observation mode.

FIG. 5A shows the status in the normal observation mode and FIG. 5B shows the status in the near observation mode.

FIG. 7A shows the status in the normal observation mode and FIG. 7B shows the status in the near observation mode.

FIG. 8A shows the status in the normal observation mode and FIG. 8B shows the status in the near observation mode.

FIG. 9A shows the status in the normal observation mode and FIG. 9B shows the status in the near observation mode.

FIG. 10A shows the status in the normal observation mode and FIG. 10B shows the status in the near observation mode.

FIG. 15 is a table in which values of the numerical conditions for the reference example and the first to seventh embodiments are listed.

DETAILED DESCRIPTION OF THE PREFERRED EMBODIMENTS

The description will be made of the mode for carrying out the present invention based on the embodiments shown with the drawings. In the optical data for each embodiment, f represents the focal length, $F_{no}$ represents the F number, $D_0$ represents the distance to the object, H represents the image height, $\omega$ represents the half field angle, $r_1, r_2, \ldots$ represent the radii of curvature of individuals surfaces, $d_1, d_2, \ldots$ represent the thickness of or air space between the lenses, $v_1, v_2, \ldots$ represent the Abbe's number of individual lenses. Also, since the image height is normalized at 1 mm for convenience of evaluation of the depth of field, values of the depth of field differ from those of actual endoscopes. However, the proportional relationship in size is maintained.

REFERENCE EXAMPLE
(Conventional Example)

Figure 1A:
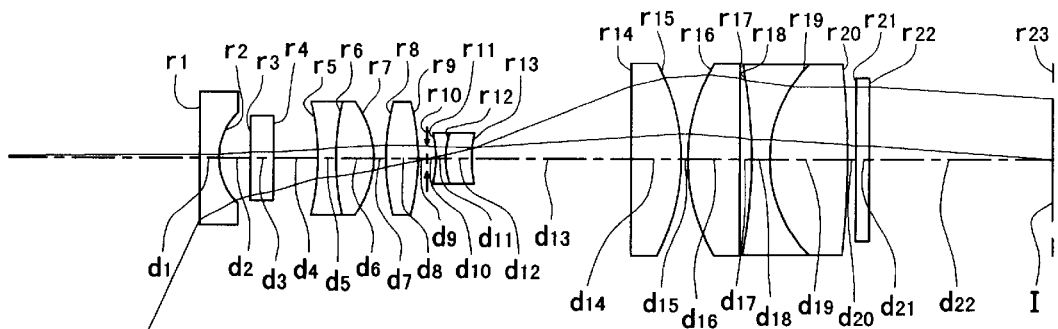
FIGS. 1A–1B show the configuration of the objective optical system of a conventional endoscope, where
Figure 1B:
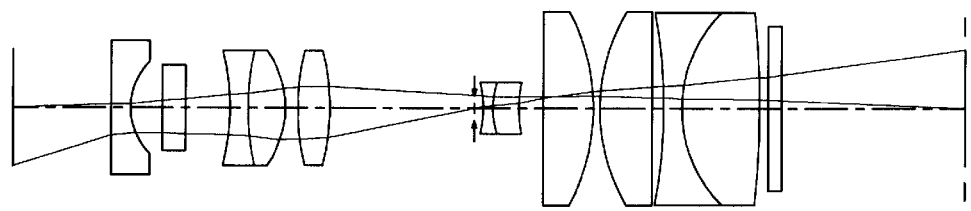

Preceding the explanation of the embodiments, the optical data of the objective optical system of the conventional endoscope shown in FIGS. 1A–1B are set forth below.

$f = 1.6 \sim 2.17$ $F_{no} = 7.97 \sim 12.57$
$2\omega = 131.1° \sim 35.3°$ $D_0 = 10.60 \sim 1.60$ $H = 1.000$

| | | | |
|---|---|---|---|
| $r_1 = \infty$ | $d_1 = 0.3227$ | $n_1 = 1.88300$ | $v_1 = 40.78$ |
| $r_2 = 1.0532$ | $d_2 = 0.5275$ | | |
| $r_3 = \infty$ | $d_3 = 0.3848$ | $n_3 = 1.51400$ | $v_3 = 57.00$ |
| $r_4 = \infty$ | $d_4 = 0.7409$ | | |
| $r_5 = -4.2301$ | $d_5 = 0.3103$ | $n_5 = 1.84666$ | $v_5 = 23.78$ |
| $r_6 = 4.2301$ | $d_6 = 0.6330$ | $n_6 = 1.51633$ | $v_6 = 64.14$ |
| $r_7 = -1.5714$ | $d_7 = 0.2172$ | | |
| $r_8 = 4.0253$ | $d_8 = 0.5275$ | $n_8 = 1.69680$ | $v_8 = 55.53$ |
| $r_9 = -4.0253$ | $d_9 = D_9$ | | |
| $r_{10} = \infty$(stop) | $d_{10} = 0.1446$ | | |
| $r_{11} = -3.0540$ | $d_{11} = 0.1862$ | $n_{11} = 0.1862$ | $v_{11} = 55.53$ |
| $r_{12} = 1.4150$ | $d_{12} = 0.4468$ | $n_{12} = 1.80518$ | $v_{12} = 25.42$ |
| $r_{13} = 2.8039$ | $d_{13} = D_{13}$ | | |
| $r_{14} = \infty$ | $d_{14} = 0.8502$ | $n_{14} = 1.72916$ | $v_{14} = 54.68$ |
| $r_{15} = -3.3221$ | $d_{15} = 0.1241$ | | |
| $r_{16} = 3.3221$ | $d_{16} = 0.8502$ | $n_{16} = 1.72916$ | $v_{16} = 54.68$ |
| $r_{17} = \infty$ | $d_{17} = 0.2023$ | | |
| $r_{18} = -9.2123$ | $d_{18} = 0.3103$ | $n_{18} = 1.84666$ | $v_{18} = 23.78$ |
| $r_{19} = 2.2156$ | $d_{19} = 1.3033$ | $n_{19} = 1.62280$ | $v_{19} = 57.05$ |
| $r_{20} = -13.8700$ | $d_{20} = 0.1179$ | | |
| $r_{21} = \infty$ | $d_{21} = 0.2482$ | $n_{21} = 1.51633$ | $v_{21} = 64.15$ |
| $r_{22} = \infty$ | $d_{22} = 3.0647$ | | |
| $r_{23} = \infty$(image surface) | | | |

| | Normal | Near |
|---|---|---|
| f | 1.06 | 2.17 |
| $D_0$ | 10.60 | 1.60 |
| $D_9$ | 0.16 | 2.44 |
| $D_{13}$ | 2.67 | 0.39 |

Next, description will be made of each embodiment of the endoscope system according to the present invention.

First Embodiment

Figure 2A:
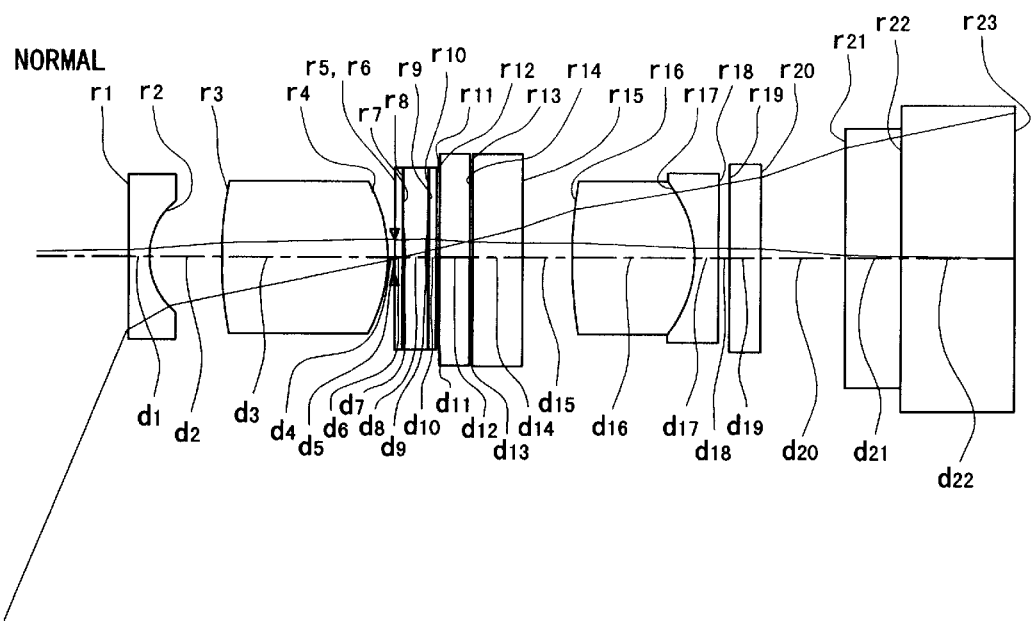
FIGS. 2A–2B show the configuration of the objective optical system according to the first embodiment of the present invention, where
Figure 2B:
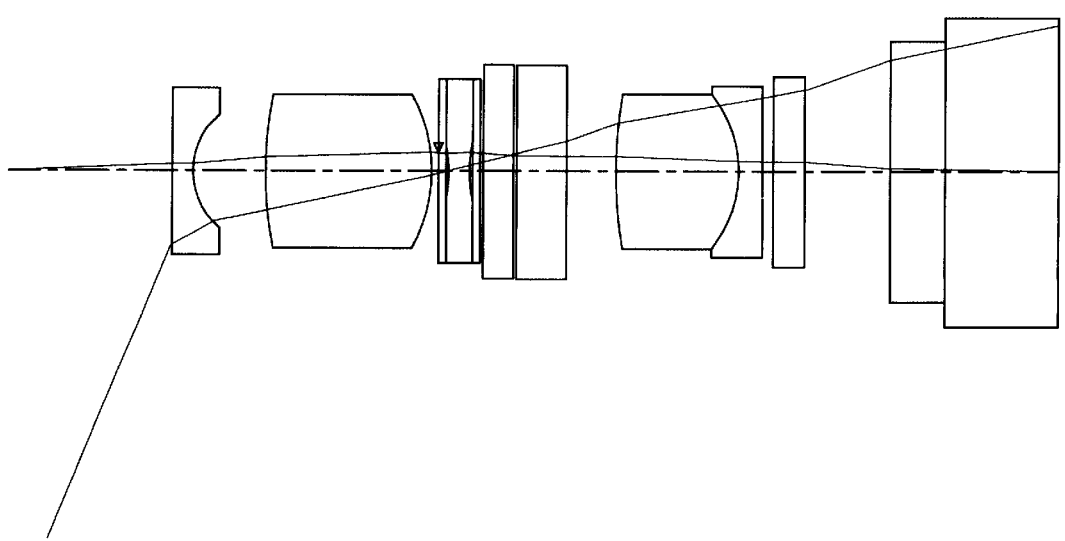

Regarding the objective optical system according to the first embodiment of the present invention, which is shown in FIGS. 2A–2B, optical data are set forth below.

$f = 1.01 \sim 0.84$ $F_{no} = 12.29 \sim 12.28$
$2\omega = 134.69° \sim 135.6°$ $D_0 = 10.80 \sim 1.08$ $H = 1.000$

| | | | |
|---|---|---|---|
| $r_1 = \infty$ | $d_1 = 0.1621$ | $n_1 = 1.88300$ | $v_1 = 40.78$ |
| $r_2 = 0.4866$ | $d_2 = 0.4764$ | | |
| $r_3 = 2.6185$ | $d_3 = 1.1178$ | $n_3 = 1.72916$ | $v_3 = 54.68$ |
| $r_4 = -1.033$ | $d_4 = 0.0322$ | | |
| $r_5 = \infty$(stop) | $d_5 = 0.0000$ | | |
| $r_6 = \infty$ | $d_6 = 0.0540$ | $n_6 = 1.74000$ | $v_6 = 28.28$ |
| $r_7 = \infty$ | $d_7 = 0.0178$ | $n_7 = 1.62000$ | $v_7 = 20.00$ |
| $r_8 = -1.8909$ | $d_8 = 0.1351$ | $n_8 = 1.56384$ | $v_8 = 60.67$ |
| $r_9 = 1.8909$ | $d_9 = 0.0178$ | $n_9 = 1.62000$ | $v_9 = 20.00$ |
| $r_{10} = \infty$ | $d_{10} = 0.0540$ | $n_{10} = 1.74000$ | $v_{10} = 28.28$ |

-continued

| | | | |
|---|---|---|---|
| $r_{11} = \infty$ | $d_{11} = 0.0162$ | | |
| $r_{12} = \infty$ | $d_{12} = 0.2161$ | $n_{12} = 1.52287$ | $v_{12} = 59.89$ |
| $r_{13} = \infty$ | $d_{13} = 0.0162$ | | |
| $r_{14} = \infty$ | $d_{14} = 0.3350$ | $n_{14} = 1.51399$ | $v_{14} = 75.00$ |
| $r_{15} = \infty$ | $d_{15} = 0.3241$ | | |
| $r_{16} = 4.1441$ | $d_{16} = 0.7982$ | $n_{16} = 1.72916$ | $v_{16} = 54.68$ |
| $r_{17} = -0.8104$ | $d_{17} = 0.1719$ | $n_{17} = 1.80518$ | $v_{17} = 25.42$ |
| $r_{18} = -116.1002$ | $d_{18} = 0.0614$ | | |
| $r_{19} = \infty$ | $d_{19} = 0.2161$ | $n_{19} = 1.52287$ | $v_{19} = 59.89$ |
| $r_{20} = \infty$ | $d_{20} = 0.5272$ | | |
| $r_{21} = \infty$ | $d_{21} = 0.3782$ | $n_{21} = 1.51633$ | $v_{21} = 64.15$ |
| $r_{22} = \infty$ | $d_{22} = 0.7675$ | $n_{22} = 1.52287$ | $v_{22} = 56.89$ |
| $r_{23} = \infty$(image surface) | | | |

| | Normal | Near |
|---|---|---|
| f | 1.01 | 0.84 |
| $D_0$ | 10.80 | 1.08 |

According to this embodiment, a liquid crystal element is arranged in the optical system. The liquid crystal element is changeable in refractive index and accordingly in the focal length as a result of change of orientation of liquid crystal molecules thereof caused by change of voltage. In the data shown above, the $6^{th}$ surface to the $11^{th}$ surface form a liquid crystal lens unit, where the $7^{th}$ and $9^{th}$ surfaces act as a liquid crystal section, which is changeable in refractive index in accordance with the status.

In this embodiment, modifying Equation (1) to be:

$$|1/X_n - 1/X_f| = 3 \cdot 3 \, \mu m \cdot F_{no}/f_L^2 \quad (6)$$

for the purpose of calculating the field of depth supposing that the resolution of the CCD corresponds to a space for three pixels arranged at 3 μm pitch, we obtain the maximum magnification of 0.405× with the depth of field of 0.86 mm. This value of magnification is not advantageous in reference to the value 1.099×, which is the maximum magnification of a conventional magnifying endoscope. However, regarding the depth of field, the above-mentioned value is about four times as wide as 0.2089 mm, or the depth of field of the conventional magnifying endoscope. Therefore, a magnifying endoscope which is friendly even to a novice user can be provided.

Figure 3:
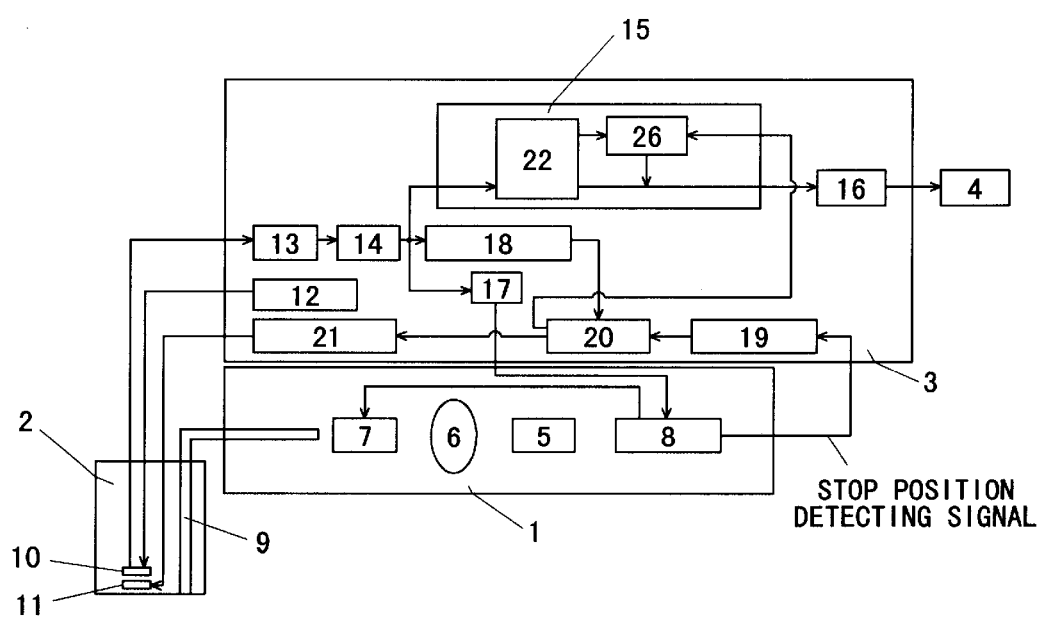
FIG. 3. is a block diagram showing the configuration of an endoscope system in which focus switching is automated.

In reference to FIG. 3, description is made of a specific configuration where focus switching is automated in an optical system as described in this embodiment or in the second to seventh embodiments. A light source unit 1 comprises a lamp 5, a light source optical system 6, a stop device 7 and a stop control device 8 and is configured so that light emanating from the lamp 5 is introduced into a light guide 9 via the light source optical system 6 and the stop device 7, to illuminate an object. Reflected light from the object is imaged on a CCD 10 via an objective optical system 11 in an endoscope 2, and then is introduced by a CCD drive circuit 12 as converted into an electric signal output from a CCD 10. The electric signal is A/D-converted by A/D converting circuit 14, then is converted into an image signal via an image generating circuit 22 included in a signal processing circuit 15, and then is D/A-converted by a D/A converting circuit 16, to be output, as an endoscopic image, to a display unit 4.

When the distance to the object is changed, amount of reflected light increases or decreases, to change brightness. Change of the signal intensity caused in this way is detected by a light adjustment means 17, and is fed back to a stop control device 8, which then drives the stop 7 to correct the change. Whereby, constant brightness can be maintained irrespective of change of distance.

Here, if the optical system of the first embodiment is employed, the focal length of the optical system can be electrically changed by a drive circuit 21 in the processor 3. Operation of the drive circuit 21 is determined by a lens control circuit 20, which controls the optical system using a light-amount-change detecting device 19 and a focus evaluation calculating circuit 18. To be specific, since change of the distance to the object causes status of the stop 7 of the light source system 1 to be changed, whether the distance to the object is changed can be determined by whether the stop 7 is driven, which is determined by the light-amount-change detecting circuit 19. On the other hand, since whether the image is in-focus can be determined by amplitude components of image enhancing signals, the focus evaluation calculating circuit 18 is able to determine whether focusing is in good condition.

In other words, the lens control circuit 20 first determines, from the information by the light-amount-change detecting circuit 19, whether the distance to the object is changed, then determines the focusing condition using the focus evaluation calculating circuit 18, and adjusts the focus of the objective optical system 11 with the drive circuit 21 so that the focusing is in good condition. In this way, focus switching is automated.

Here, in an optical system such as disclosed in the first embodiment, since the focal length in the near observation mode is shorter than the focal length in the normal observation mode, the field angle becomes wider. Resultantly, problems are raised in that performance of the curvature of field is degraded on the margin of the image or in that shortage of amount of marginal rays occurs to make the field dim.

According to the present invention, a control device is provided so as to set, at least in the near observation mode, the ratio of image information α possibly appearing on the solid-state image sensor to image information β displayed on the display unit to be:

$$\alpha/\beta \geq 1 \quad (7)$$

for the purpose of preventing deterioration regarding image quality or amount of marginal rays.

Since these problems relate to degradation of image quality on the margin of the field, if the near observation mode is selected, displaying less information on the image display unit than the original information to prevent marginal image information from being displayed would solve the problems.

In FIG. 3, an image magnifying circuit 26 in the signal processing circuit 15 works for this purpose. Receiving the decision by the lens control circuit 20, this circuit 15 determines which of the near observation mode and the normal observation mode is selected, to feed the result back to the image information. Since this function automatically prevents undesirable information for display from being displayed on the display unit, a medical doctor is able to make diagnosis by concentrating on the portion of interest without special manipulation. In this way, operability is very much improved.

Also, since degradation of the image on the margin occurs over 75% region of the surface, it is preferred that magnification given by the image magnifying circuit 26 is designed to satisfy:

$$\alpha/\beta \geq 1.25 \quad (8)$$

and, in addition, that the center point of the displayed image on the image display unit corresponds to a point existing inside the center 25% region of the possible image information on the solid-state image sensor, because this arrangement at least reduces the probability of the degraded region being observed.

Second Embodiment

Figure 4A:
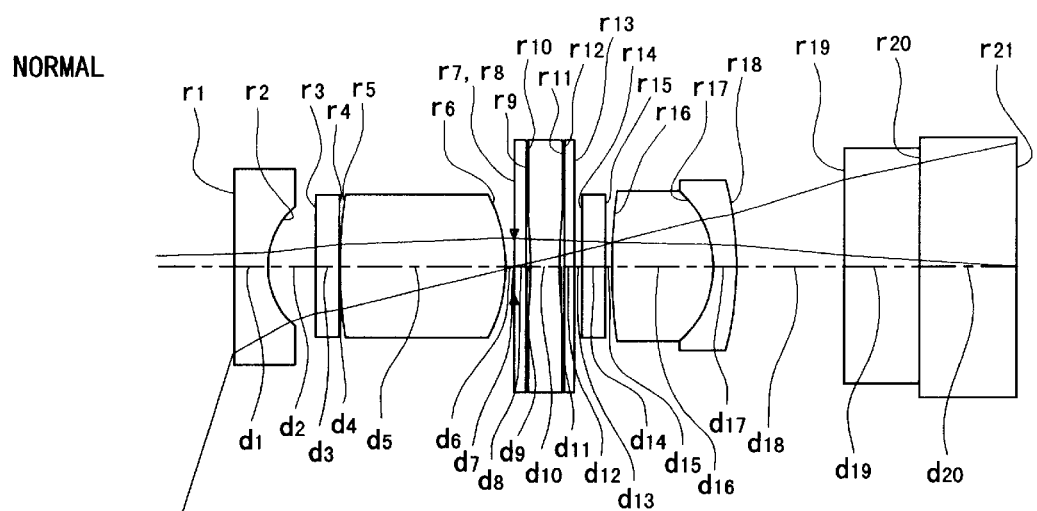
FIGS. 4A–4B show the configuration of the objective optical system according to the second embodiment of the present invention, where
Figure 4B:
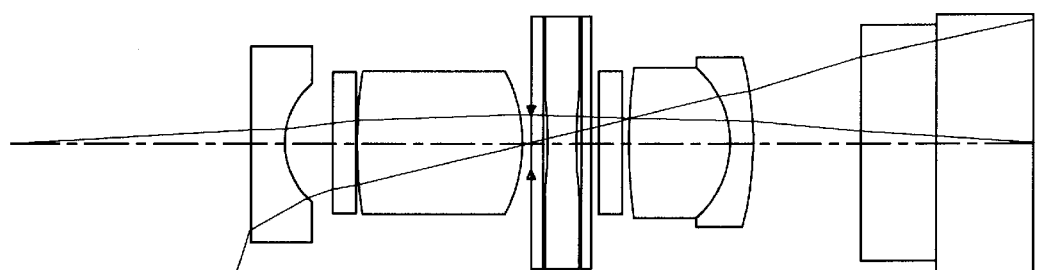

Regarding the objective optical system according to the second embodiment of the present invention, which is shown in FIGS. 4A–4B, optical data are set forth below.

| $f = 0.96 \sim 0.89$ | $F_{no} = 5.63 \sim 5.61$ | | |
|---|---|---|---|
| $2\omega = 145.8° \sim 149.8°$ | $D_0 = 12.30 \sim 2.20$ | $H = 1.000$ | |
| $r_1 = \infty$ | $d_1 = 0.2854$ | $n_1 = 1.88300$ | $v_1 = 40.78$ |
| $r_2 = 0.6261$ | $d_2 = 0.3777$ | | |
| $r_3 = \infty$ | $d_3 = 0.1924$ | $n_3 = 1.51399$ | $v_3 = 75.00$ |
| $r_4 = \infty$ | $d_4 = 0.0103$ | | |
| $r_5 = 3.6661$ | $d_5 = 1.3155$ | $n_5 = 1.77250$ | $v_5 = 49.60$ |
| $r_6 = -1.2411$ | $d_6 = 0.0621$ | | |
| $r_7 = \infty$(stop) | $d_7 = 0.0000$ | | |
| $r_8 = \infty$ | $d_8 = 0.0944$ | $n_8 = 1.74000$ | $v_8 = 28.28$ |
| $r_9 = \infty$ | $d_9 = 0.0312$ | $n_9 = 1.52400$ | $v_9 = 30.20$ |
| $r_{10} = -5.3843$ | $d_{10} = 0.2361$ | $n_{10} = 1.56384$ | $v_{10} = 60.67$ |
| $r_{11} = 5.3843$ | $d_{11} = 0.0312$ | $n_{11} = 1.52400$ | $v_{11} = 30.20$ |
| $r_{12} = \infty$ | $d_{12} = 0.0944$ | $n_{12} = 1.74000$ | $v_{12} = 28.28$ |
| $r_{13} = \infty$ | $d_{13} = 0.0504$ | | |
| $r_{14} = \infty$ | $d_{14} = 0.1924$ | $n_{14} = 1.51399$ | $v_{14} = 75.00$ |
| $r_{15} = \infty$ | $d_{15} = 0.0490$ | | |
| $r_{16} = 3.5817$ | $d_{16} = 0.8067$ | $n_{16} = 1.69680$ | $v_{16} = 55.53$ |
| $r_{17} = -0.7899$ | $d_{17} = 0.1737$ | $n_{17} = 1.84666$ | $v_{17} = 23.78$ |
| $r_{18} = -3.1151$ | $d_{18} = 0.8206$ | | |
| $r_{19} = \infty$ | $d_{19} = 0.6205$ | $n_{19} = 1.51633$ | $v_{19} = 64.15$ |
| $r_{20} = \infty$ | $d_{20} = 0.7757$ | $n_{20} = 1.52287$ | $v_{20} = 59.89$ |
| $r_{21} = \infty$(image surface) | | | |

| | Normal | Near |
|---|---|---|
| f | 0.96 | 0.89 |
| $D_0$ | 12.30 | 2.20 |

According to this embodiment also, a liquid crystal element is arranged in the optical system. The liquid crystal element is changeable in refractive index and accordingly in the focal length as a result of change of orientation of liquid crystal molecules thereof causedby change of voltage. According to this embodiment, the $8^{th}$ surface to the $13^{th}$ surface form a liquid crystal lens unit, where the $9^{th}$ and $11^{th}$ surfaces act as a liquid crystal section, which is changeable in refractive index in accordance with the status.

Calculating the field of depth supposing that the resolution of the CCD corresponds to a space for three pixels arranged at 3 μm pitch as done in the first embodiment, we obtain the maximum magnification of 0.405× with the depth of field of 0.86 mm. According to this embodiment also, the value of magnification is not advantageous in reference to the value 1.099×, which is the maximum magnification of a conventional magnifying endoscope, while the value of depth of field is about four times as wide as 0.2089 mm, or the depth of field of the conventional magnifying endoscope. Therefore, a magnifying endoscope which is friendly even to a novice user can be provided.

In this embodiment, more refined design is made in filter arrangement than in the first embodiment. According to the first embodiment, interference-type laser cutoff filters are arranged to form the $12^{th}$ and $13^{th}$ surfaces and the $19^{th}$ and $2^{th}$ surfaces, and an absorption-type infrared cutoff filter is arranged to form the $14^{th}$ and $15^{th}$ surfaces. Endoscopes would be used in laser treatment application. Since a CCD is vulnerable to laser light, two laser-cutoff surfaces are necessary. In addition, an attempt to adapt the endoscope to two kinds of laser light raises a requirement for another two laser-cutoff surfaces. To sum up, it is necessary to provide two interference-type filters, each of which is provided with laser cutoff filter surfaces arranged on both the surfaces thereof. On the other hand, at least one absorption-type color filter is needed for the purpose of assuring color reproductivity as required for an endoscope. However, according to the second embodiment, absorption-type infrared cutoff filters that are thinner than the filters of the first embodiment are arranged to form the $2^{nd}$ and $3_{rd}$ surfaces and the $14^{th}$ and $15^{th}$ surfaces, on each of which an interference-type laser cutoff filter is arranged, to save a space accommodating one filter while satisfying the required specification.

Third Embodiment

Figure 5A:
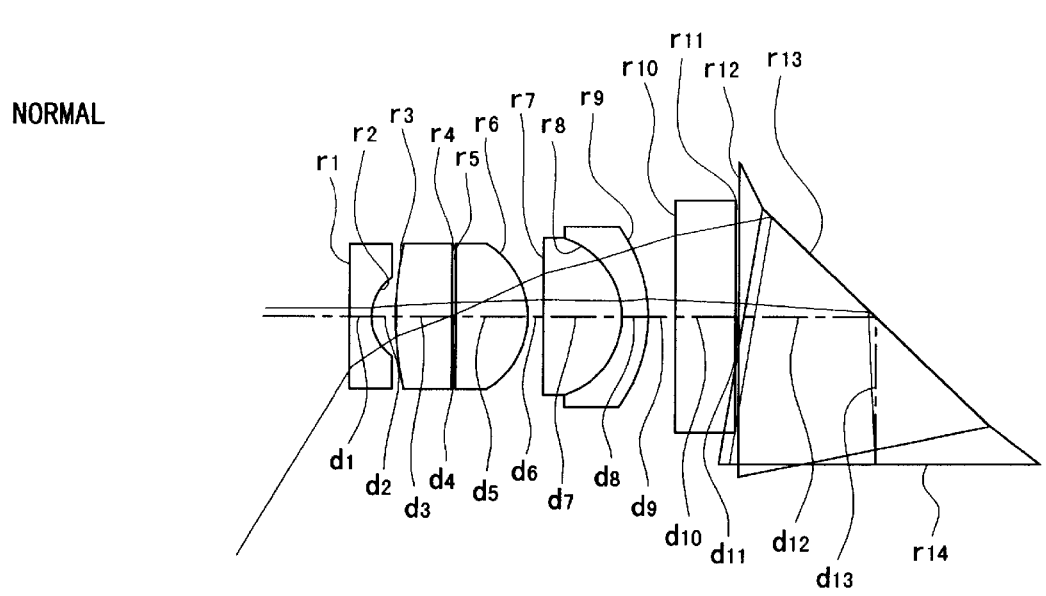
FIGS. 5A–5B show the configuration of the objective optical system according to the third embodiment of the present invention, where
Figure 5B:
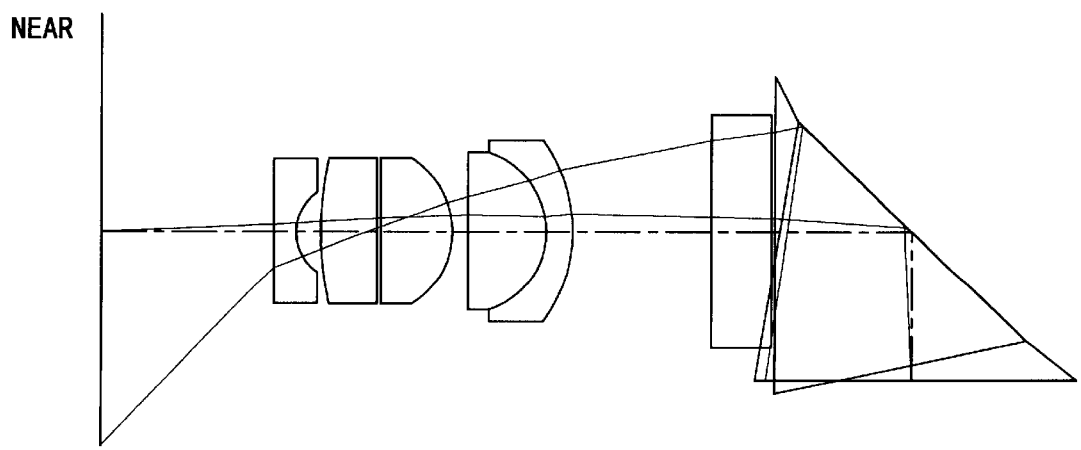

Regarding the objective optical system according to the third embodiment of the present invention, which is shown in FIGS. 5A–5B, optical data are set forth below.

| $f = 1.06 \sim 1.06$ | $F_{no} = 10.41 \sim 12.78$ | | |
|---|---|---|---|
| $2\omega = 117.1° \sim 91.3°$ | $D_0 = 11.00 \sim 1.20$ | $H = 1.000$ | |
| $r_1 = \infty$ | $d_1 = 0.1534$ | $n_1 = 1.57135$ | $v_1 = 52.95$ |
| $r_2 = 0.3578$ | $d_2 = 0.1678$ | | |
| $r_3 = 1.8555$ | $d_3 = 0.4111$ | $n_3 = 1.80518$ | $v_3 = 25.42$ |
| $r_4 = \infty$ | $d_4 = 0.0163$ | | |
| $r_5 = \infty$ | $d_5 = 0.5018$ | $n_5 = 1.48749$ | $v_5 = 70.23$ |
| $r_6 = -0.5889$ | $d_6 = 0.1217$ | | |
| $r_7 = \infty$ | $d_7 = 0.5332$ | $n_7 = 1.53996$ | $v_7 = 59.46$ |
| $r_8 = -0.5918$ | $d_8 = 0.1775$ | $n_8 = 1.80518$ | $v_8 = 25.42$ |
| $r_9 = -1.1384$ | $d_9 = D_9$ | | |
| $r_{10} = \infty$ | $d_{10} = 0.4558$ | $n_{10} = 1.51633$ | $v_{10} = 64.14$ |
| $r_{11} = \infty$ | $d_{11} = 0.0212$ | | |
| $r_{12} = \infty$ | $d_{12} = 0.9357$ | $n_{12} = 1.51633$ | $v_{12} = 64.14$ |
| $r_{13} = \infty$ | $d_{13} = -1.0322$ | $n_{13} = 1.51633$ | $v_{13} = 64.14$ |
| $r_{14} = \infty$(image surface) | | | |

| | Normal | Near |
|---|---|---|
| f | 1.06 | 1.06 |
| $D_0$ | 11.00 | 1.20 |
| $D_9$ | 0.20 | 1.01 |

This embodiment is configured so that the solid-state image sensor is driven to follow shift of the image position, which is caused by change of the working distance. As to this embodiment, calculating the field of depth supposing that the resolution of the CCD corresponds to a space for three pixels arranged at 3 μm pitch, we obtain the maximum magnification of 0.969× with the depth of field of 0.32 mm. Although the depth of field is rather narrow in reference to the first or second embodiment, the value of the magnification is close to that of the conventional endoscope. Also, the configuration in which the exit pupil of the optical system is disposed on the object side of the solid-state image sensor and the solid-state image sensor itself can be driven to move as in this embodiment allows the magnification to be increased without change of the focal length and thus is advantageous for a magnifying endoscope.

Figure 6:
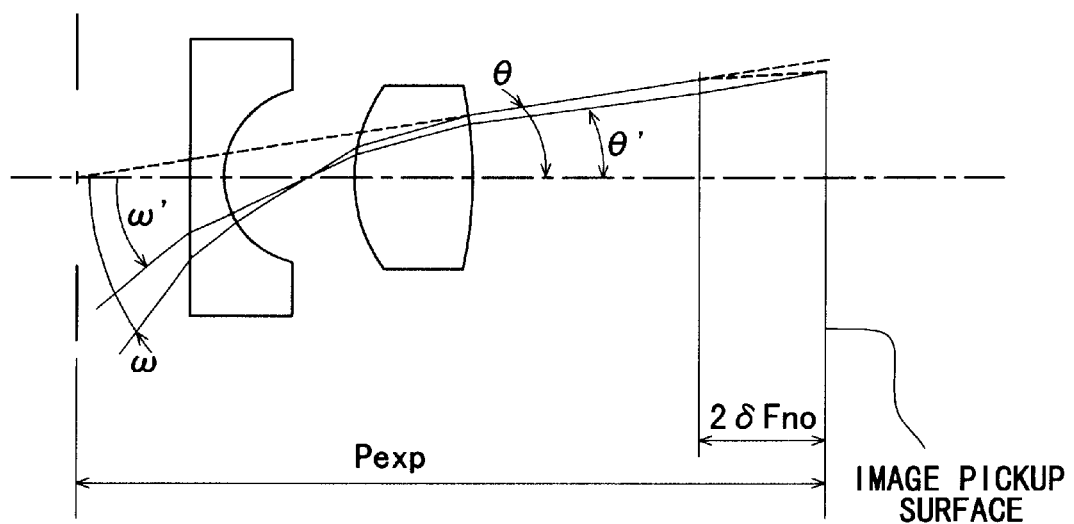
FIG. 6 is a view to explain change of incident angle at the solid-state image sensor in accordance with the working distance.

As shown in FIG. 6, if the exit pupil position $P_{exp}$ satisfies the following condition in reference to the position of the solid-state image sensor as an origin:

$$P_{exp} < 0 \qquad (9)$$

the image position is shifted by $2\delta F_{no}$ as the working distance becomes $WD_{tele}$, and the incident angle of a ray incident at the maximum image height on the solid-state image sensor, which has been moved to follow the image position, is changed to $\Theta'$, where the incident angle of a ray incident at the maximum image height on the solid-state image sensor under the condition where the working distance is $WD_{wide}$ is $\theta$. On the other hand, since it is known that endoscope optical systems in general are fθ-type optical systems, the half field angle ω' after the image position shift is given by:

$$\omega' = \omega \cdot \theta'/\theta \quad (10)$$

where the half field angle before the image position shift, or the half field angle associated with the incident angle θ is ω.

Now, the condition of the exit pupil gives:

$$\theta'/\theta < 1 \quad (11)$$

and then $$\omega' < \omega \quad (12)$$

In other words, satisfaction of Condition (9) allows the optical magnification β to be higher without change of the focal length.

On the basis of this concept, the third embodiment is configured to assure the minimum necessary field of depth and as large a magnification as possible without change of the focal length $f_L$, or under the condition $f_{Lwide} = f_{Ltele}$.

Fourth Embodiment

Figure 7A:
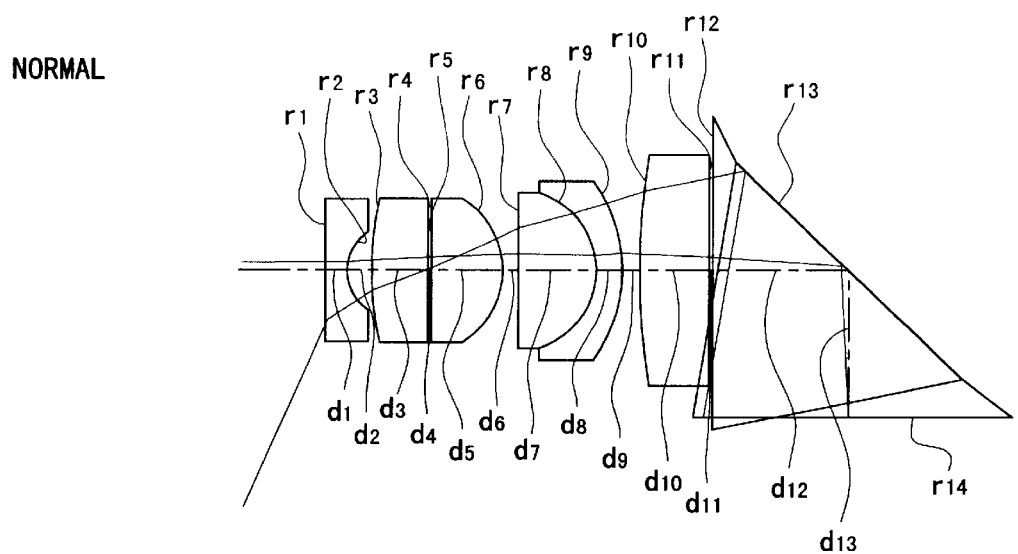
FIGS. 7A–7B show the configuration of the objective optical system according to the fourth embodiment of the present invention, where
Figure 7B:
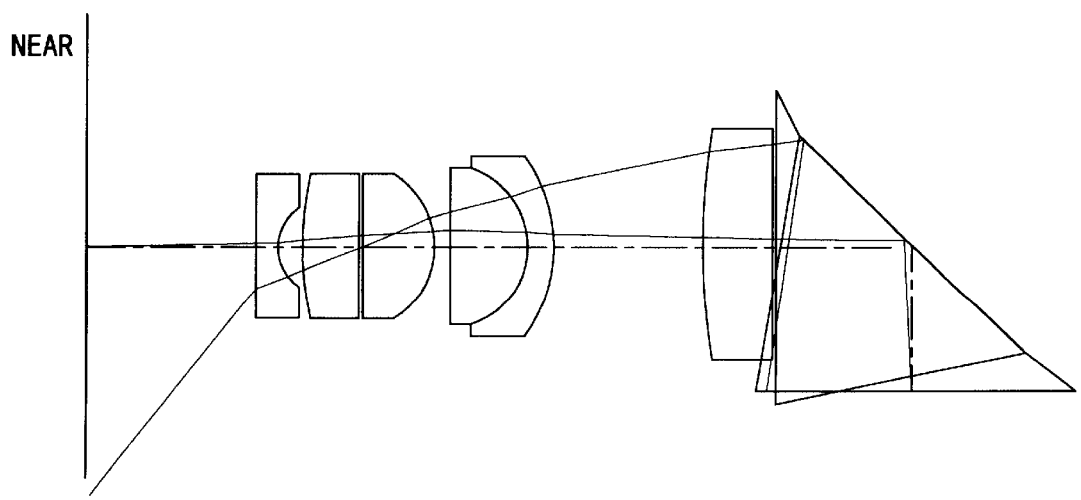

Regarding the objective optical system according to the fourth embodiment of the present invention, which is shown in FIGS. 7A–7B, optical data are set forth below.

| f = 0.97 ~ 1.01 | $F_{no}$ = 9.55 ~ 11.72 | | |
|---|---|---|---|
| 2ω = 131.3° ~ 100.4° | $D_0$ = 10.80 ~ 1.08 | H = 1.000 | |
| $r_1 = \infty$ | $d_1 = 0.1534$ | $n_1 = 1.57135$ | $v_1 = 52.95$ |
| $r_2 = 0.3578$ | $d_2 = 0.1678$ | | |
| $r_3 = 1.8555$ | $d_3 = 0.4111$ | $n_3 = 1.80518$ | $v_3 = 25.42$ |
| $r_4 = \infty$ | $d_4 = 0.0163$ | | |
| $r_5 = \infty$ | $d_5 = 0.5018$ | $n_5 = 1.48749$ | $v_5 = 70.23$ |
| $r_6 = -0.5889$ | $d_6 = 0.1217$ | | |
| $r_7 = \infty$ | $d_7 = 0.5332$ | $n_7 = 1.53996$ | $v_7 = 59.46$ |
| $r_8 = -0.5918$ | $d_8 = 0.1775$ | $n_8 = 1.80518$ | $v_8 = 25.42$ |
| $r_9 = -1.1384$ | $d_9 = D_9$ | | |
| $r_{10} = 10.0000$ | $d_{10} = 0.4558$ | $n_{10} = 1.51633$ | $v_{10} = 64.14$ |
| $r_{11} = \infty$ | $d_{11} = 0.0212$ | | |
| $r_{12} = \infty$ | $d_{12} = 0.9357$ | $n_{12} = 1.51633$ | $v_{12} = 64.14$ |
| $r_{13} = \infty$ | $d_{13} = -1.0322$ | $n_{13} = 1.51633$ | $v_{13} = 64.14$ |
| $r_{14} = \infty$ | $d_{14} = 0.0150$ | | |

| | Normal | Near |
|---|---|---|
| f | 0.97 | 1.01 |
| $D_0$ | 11.00 | 1.20 |
| $D_9$ | 0.11 | 0.91 |

The fourth embodiment is configured so that a field lens is incorporated into the magnifying endoscope according to the third embodiment. Calculating the field of depth and the magnification supposing that the resolution of the CCD corresponds to a space for three pixels arranged at 3 μm pitch, we obtain the maximum magnification of 0.893× with the depth of field of 0.345 mm. In general, a field lens is used for the purpose of greatly changing the pupil position. However, the field lens according to this embodiment has very little curvature and thus is not used for pupil position control. According to this embodiment:

$$f_{wide} = 0.9729 < f_{tele} = 1.01174 \quad (13)$$

which expression is inconsistent with Condition (3). However, this embodiment substantially utilizes the present invention. To make this fact clear, according to the present invention, allowable variation range of the focal length is specified in consideration of the exit pupil position as follows:

$$f_{wide} \geq 1.1 \cdot f_{tele} \quad (14)$$

$$P_{exp} < 0 \quad (15)$$

Fifth Embodiment

Figure 8A:
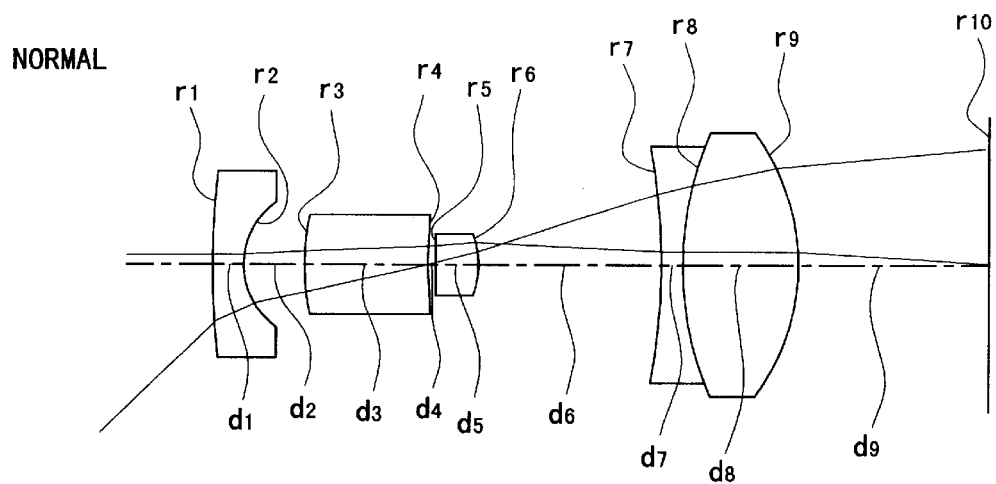
FIGS. 8A–8B show the configuration of the objective optical system according to the fifth embodiment of the present invention, where
Figure 8B:
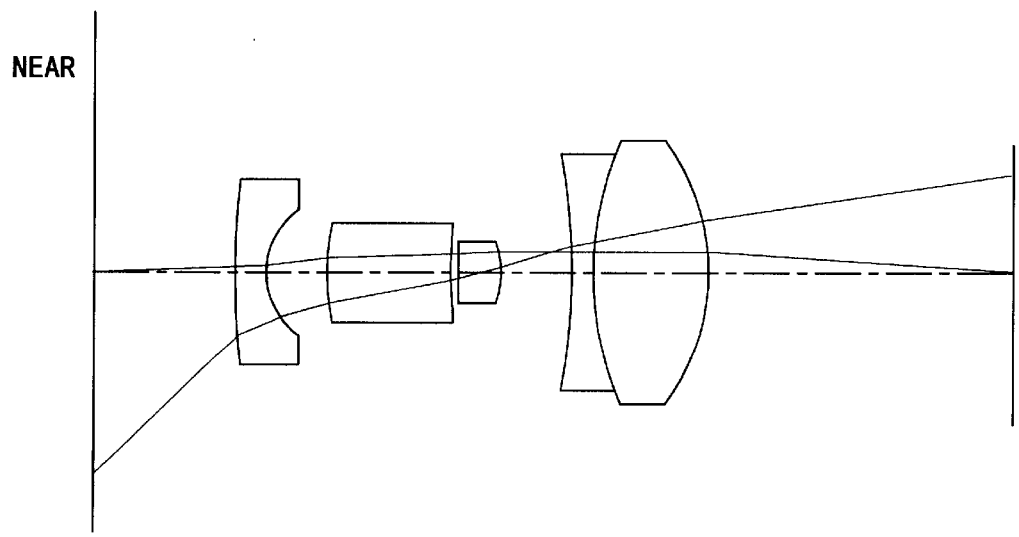

Regarding the objective optical system according to the fifth embodiment of the present invention, which is shown in FIGS. 8A–8B, optical data are set forth below.

| f = 1.04 ~ 0.88 | $F_{no}$ = 7.83 ~ 7.53 | | |
|---|---|---|---|
| 2ω = 86.5° ~ 88.7° | $D_0$ = 11.00 ~ 1.00 | H = 1.000 | |
| $r_1 = 5.5556$ | $d_1 = 0.2222$ | $n_1 = 1.88300$ | $v_1 = 40.76$ |
| $r_2 = 0.4912$ | $d_2 = 0.4202$ | | |
| $r_3 = 1.2694$ | $d_3 = 0.8628$ | $n_3 = 1.84666$ | $v_3 = 23.78$ |
| $r_4 = 1.1962$ | $d_4 = 0.0556$ | | |
| $r_5 = 4.4257$ | $d_5 = 0.2778$ | $n_5 = 1.77250$ | $v_5 = 49.60$ |
| $r_6 = -0.8038$ | $d_6 = D_6$ | | |
| $r_7 = -7.4387$ | $d_7 = 0.1667$ | $n_7 = 1.84666$ | $v_7 = 23.78$ |
| $r_8 = 2.1819$ | $d_8 = 0.7778$ | $n_8 = 1.72916$ | $v_8 = 54.68$ |
| $r_9 = -1.5714$ | $d_9 = D_9$ | | |
| $r_{10} = \infty$ (image surface) | | | |

| | Normal | Near |
|---|---|---|
| f | 1.04 | 0.88 |
| $D_0$ | 11.00 | 1.00 |
| $D_6$ | 1.28 | 0.47 |
| $D_9$ | 0.31 | 2.11 |

This embodiment is configured so that lenses in the optical system are driven to move for changing the focal length. According to this embodiment, the focal length $f_L$ has a smaller value in the magnifying observation mode than in the normal observation mode. Assuming that the resolution of the CCD corresponds to a space for three pixels arranged at 3 μm pitch, we calculate that the maximum magnification is 0.735× with the depth of field of 0.32 mm, which is wider than in the case of the conventional magnifying endoscope.

According to this embodiment, curvature of field in the magnifying observation mode is precluded by the meniscus structure of the most object-side surfaces of the objective lens where the convex surfaces are directed toward the object side. If the lens is located near the object while the field angle remains wide, a great difference in the optical path length to the object is generated between the central portion and the marginal portion, and resultantly curvature of the field on the marginal portion remains undercorrected. Shifting the off-axial principal point to the axial principal point would solve this problem. To this end, it is effective to form the most object-side surfaces of the objective lens as a meniscus structure directing the convex surfaces toward the object side.

Such a configuration is effectively applicable to the remaining embodiments of the present invention, as a matter of course.

Sixth Embodiment

Figure 9A:
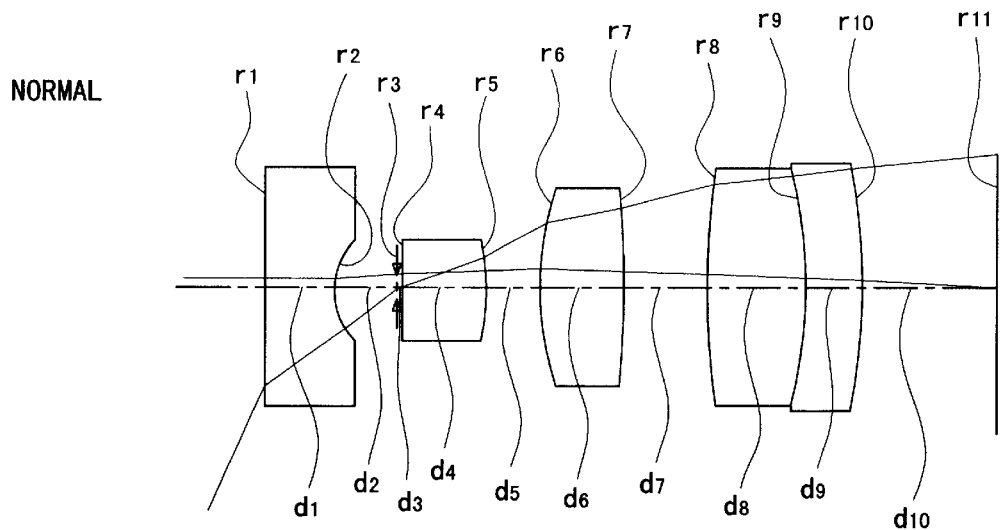
FIGS. 9A–9B show the configuration of the objective optical system according to the sixth embodiment of the present invention, where
Figure 9B:
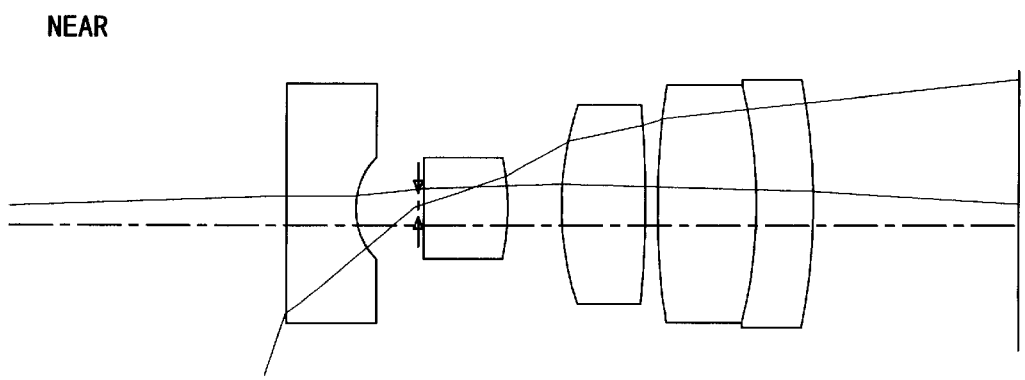

Regarding the objective optical system according to the sixth embodiment of the present invention, which is shown in FIGS. 9A–9B, optical data are set forth below.

| f = 1.16 ~ 1.07 | | $F_{no}$ = 8.14 ~ 8.23 | |
|---|---|---|---|
| 2ω = 130.7° ~ 148.2° | | $D_0$ = 25.00 ~ 2.00 | H = 1.000 |
| $r_1$ = ∞ | $d_1$ = 0.5000 | $n_1$ = 1.51633 | $v_1$ = 64.14 |
| $r_2$ = 0.5000 | $d_2$ = 0.4500 | | |
| $r_3$ = ∞(stop) | $d_3$ = 0.0300 | | |
| $r_4$ = ∞ | $d_4$ = 0.6000 | $n_4$ = 1.88300 | $v_4$ = 40.76 |
| $r_5$ = −1.5000 | $d_5$ = 0.4000 | | |
| $r_6$ = 2.5000 | $d_6$ = 0.6000 | $n_6$ = 1.69680 | $v_6$ = 55.53 |
| $r_7$ = −8.0000 | $d_7$ = $D_7$ | | |
| $r_8$ = 7.8431 | $d_8$ = 0.7000 | $n_8$ = 1.69680 | $v_8$ = 55.53 |
| $r_9$ = −3.3460 | $d_9$ = 0.4000 | $n_9$ = 1.78472 | $v_9$ = 25.68 |
| $r_{10}$ = −5.7819 | $d_{10}$ = $D_{10}$ | | |
| $r_{11}$ = ∞(image surface) | | | |

| | Normal | Near |
|---|---|---|
| f | 1.16 | 1.07 |
| $D_0$ | 25.00 | 2.00 |
| $D_7$ | 0.60 | 0.10 |
| $D_{10}$ | 0.96 | 1.46 |

This embodiment also is configured so that lenses in the optical system are driven to move for changing the focal length. According to this embodiment, the focal length $f_L$ has a smaller value in the magnifying observation mode than in the normal observation mode. Assuming that the resolution of the CCD corresponds to a space for three pixels arranged at 3 μm pitch, we calculate that the maximum magnification is 0.515× with the depth of field of 0.76 mm, which is wider than in the case of the conventional magnifying endoscope.

Seventh Embodiment

Figure 10A:
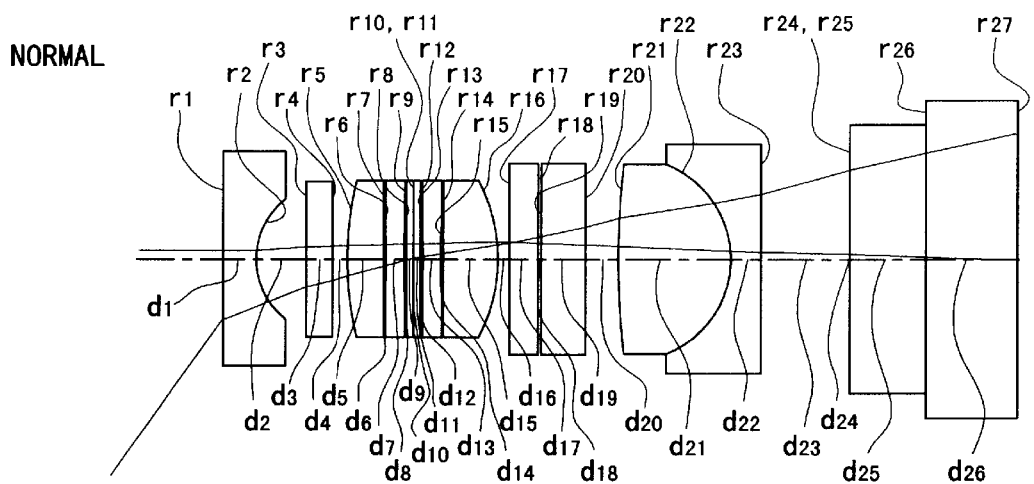
FIGS. 10A–10B show the configuration of the objective optical system according to the seventh embodiment of the present invention, where
Figure 10B:
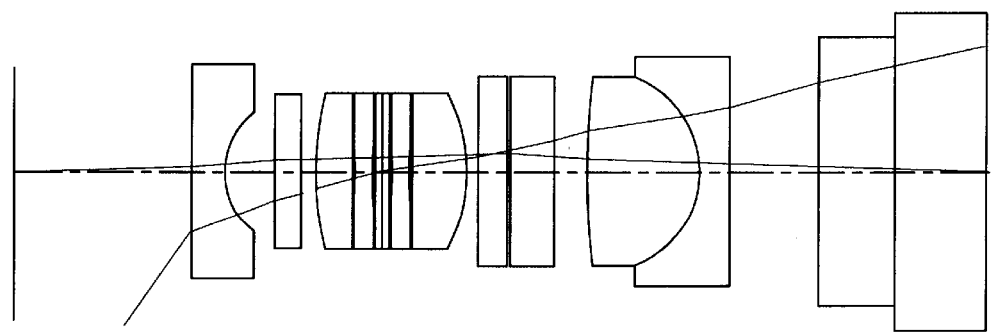

Regarding the objective optical system according to the seventh embodiment of the present invention, which is shown in FIGS. 10A–10B, optical data are set forth below.

| f = 1.10 ~ 0.95 | | $F_{no}$ = 11.01 ~ 11.39 | |
|---|---|---|---|
| 2ω = 109.9° ~ 109.2° | | $D_0$ = 10.60 ~ 1.30 | H = 1.000 |
| $r_1$ = ∞ | $d_1$ = 0.2701 | $n_1$ = 1.88300 | $v_1$ = 40.78 |
| $r_2$ = 0.5520 | $d_2$ = 0.3339 | | |
| $r_3$ = ∞ | $d_3$ = 0.2161 | $n_3$ = 1.52287 | $v_3$ = 59.89 |
| $r_4$ = ∞ | $d_4$ = 0.0982 | | |
| $r_5$ = 1.8909 | $d_5$ = 0.2701 | $n_5$ = 1.88300 | $v_5$ = 40.76 |
| $r_6$ = ∞ | $d_6$ = 0.0124 | $n_6$ = 1.52400 | $v_6$ = 30.20 |
| $r_7$ = −5.4025 | $d_7$ = 0.1351 | $n_7$ = 1.56384 | $v_7$ = 60.67 |
| $r_8$ = 5.4025 | $d_8$ = 0.0124 | $n_8$ = 1.52400 | $v_8$ = 30.20 |
| $r_9$ = ∞ | $d_9$ = 0.0540 | $n_9$ = 1.74000 | $v_9$ = 28.28 |
| $r_{10}$ = ∞ | $d_{10}$ = 0.0000 | | |
| $r_{11}$ = ∞ | $d_{11}$ = 0.0540 | $n_{11}$ = 1.74000 | $v_{11}$ = 28.28 |
| $r_{12}$ = ∞ | $d_{12}$ = 0.0124 | $n_{12}$ = 1.52400 | $v_{12}$ = 30.20 |
| $r_{13}$ = −5.4025 | $d_{13}$ = 0.1351 | $n_{13}$ = 1.56384 | $v_{13}$ = 60.67 |
| $r_{14}$ = 5.4025 | $d_{14}$ = 0.0124 | $n_{14}$ = 1.52400 | $v_{14}$ = 30.20 |
| $r_{15}$ = ∞ | $d_{15}$ = 0.4118 | $n_{15}$ = 1.88300 | $v_{15}$ = 40.76 |
| $r_{16}$ = −1.2651 | $d_{16}$ = 0.0730 | | |
| $r_{17}$ = ∞ | $d_{17}$ = 0.2161 | $n_{17}$ = 1.52287 | $v_{17}$ = 59.89 |
| $r_{18}$ = ∞ | $d_{18}$ = 0.0162 | | |
| $r_{19}$ = ∞ | $d_{19}$ = 0.3350 | $n_{19}$ = 1.51399 | $v_{19}$ = 75.00 |
| $r_{20}$ = ∞ | $d_{20}$ = 0.2230 | | |
| $r_{21}$ = 7.9626 | $d_{21}$ = 0.7982 | $n_{21}$ = 1.75500 | $v_{21}$ = 52.32 |
| $r_{22}$ = −0.7740 | $d_{22}$ = 0.2420 | $n_{22}$ = 1.84666 | $v_{22}$ = 23.78 |
| $r_{23}$ = ∞ | $d_{23}$ = 0.6194 | | |
| $r_{24}$ = ∞ | $d_{24}$ = 0.0000 | | |
| $r_{25}$ = ∞ | $d_{25}$ = 0.5402 | $n_{25}$ = 1.51633 | $v_{25}$ = 64.15 |
| $r_{26}$ = ∞ | $d_{26}$ = 0.6753 | $n_{22}$ = 1.52287 | $v_{22}$ = 59.89 |
| $r_{27}$ = ∞(image surface) | | | |

| | Normal | Near |
|---|---|---|
| f | 1.10 | 0.95 |
| $D_0$ | 10.60 | 1.30 |

According to this embodiment, two liquid-crystal elements as used in the first or second embodiment are employed. It is necessary to increase curvature and accordingly to increase optical power of a liquid crystal element for the purpose of enhancing focus adjustment performance. However, if a liquid crystal lens reduces its radius of curvature under the condition where the effective diameter thereof is kept constant, the thickness of the liquid crystal layer becomes greater. In general, as the liquid crystal layer becomes thicker, the response speed is lowered, which is unfavorable. Therefore, according to this embodiment, a plurality of such liquid crystal elements are used so that the required power is distributed among individual elements. Accordingly, a high optical power is obtained in the entire system while the liquid crystal is able to achieve high response speed with a large radius of curvature because a power assigned to each element is small. While two elements are used to generate an optical power, it is possible to apply a voltage only to one of them so as to utilize half the optical power.

Regarding the magnification and the depth of field of the seventh embodiment, supposing that the resolution of the CCD corresponds to a space for three pixels arranged at 3 μm pitch, we calculate that the maximum magnification is 0.749× with the depth of field of 0.495 mm.

Eighth Embodiment

Figure 11:
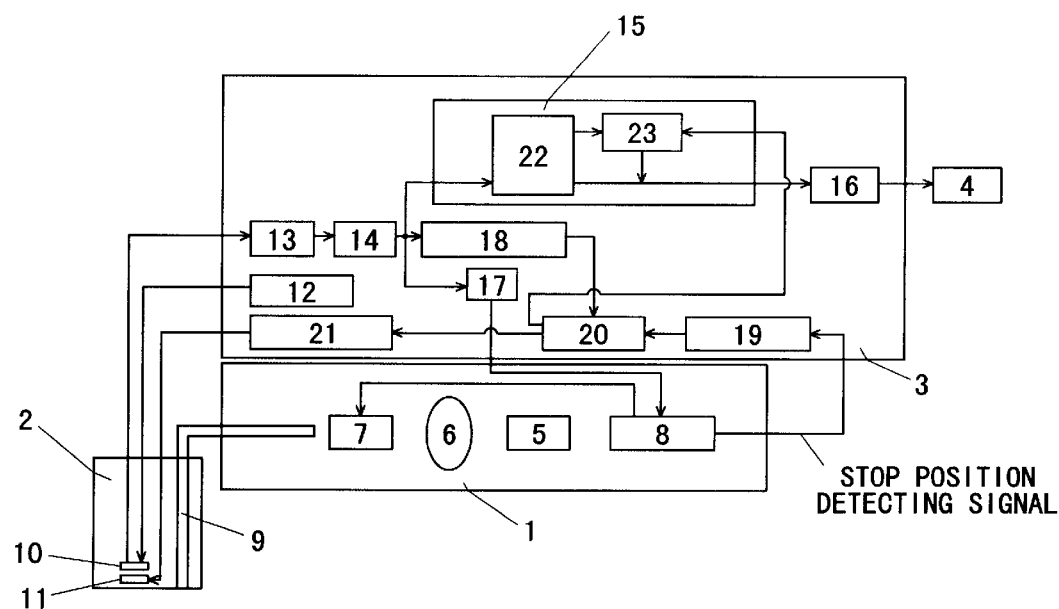
FIG. 11 is a block diagram showing the entire configuration of the endoscope system according to the eighth embodiment of the present invention.

FIG. 11 is an entire configuration diagram of an endoscope system according to the eighth embodiment of the present invention. This embodiment differs from the control system shown in FIG. 3 in that the drive circuit 21 is specified to be a liquid-crystal drive circuit and in that the image magnifying circuit 26 is replaced by an image enhancing circuit 23. However, since flow of the image information substantially is the same as the first embodiment explained in reference to FIG. 3, a detailed explanation is omitted. According to this embodiment, in response to the decision by the lens control circuit 20, which of the near observation mode and the normal observation mode is selected is determined, and the result is fed back to the image enhancing circuit 23. In accordance with this signal, the image enhancing circuit 23 processes an image signal selected by the image generating circuit 22 so that the optimum enhancing mode is selected for each of the near observation mode and the normal observation mode. In this case, configuration may be made so that selection of the image enhancing mode is made extraneously or so that, in accordance with given peculiar information on each endoscope, the image enhancing mode optimized for each endoscope is selected. Also, regarding image processing in the near observation mode, since tissues such as minute blood vessels and mucous membrane structure of a living body are observed at a high magnification, it is preferred to enhance a relatively low frequency so as to achieve image processing optimized for a frequency peculiar to each structure. In contrast, since a web pattern of submucous blood vessels is observed at a low magnification, it is preferred to enhance a high frequency to achieve image processing optimized for the normal observation mode.

Here, a frequency to be enhanced is specified as follows. Where the sampling frequency of a CCD is $f_S$, the limit of resolution, or Nyquist rate $f_n$ is given by:

$$f_n = f_s/2 \tag{16}$$

According to the present invention, the high frequency and the low frequency are defined as follows. If a spatial frequency f satisfies:

$$0 < f < f_n/2 = f_s/4 \tag{17}$$

f is defined as a low frequency. If a spatial frequency f satisfies:

$$f_n/2 = f_s/4 < f < f_n = f_s/2 \tag{18}$$

f is defined as a high frequency.

Arranging of a peak frequency for enhancement in each frequency band is required for optimum image processing. Configuration may be made so that several kinds of such image processing modes are prepared and selection out of these options are made extraneously, or so that, upon determination of the type of the endoscope currently connected with the processor, an image processing means optimized for this endoscope is selected.

Ninth Embodiment

Figure 12:
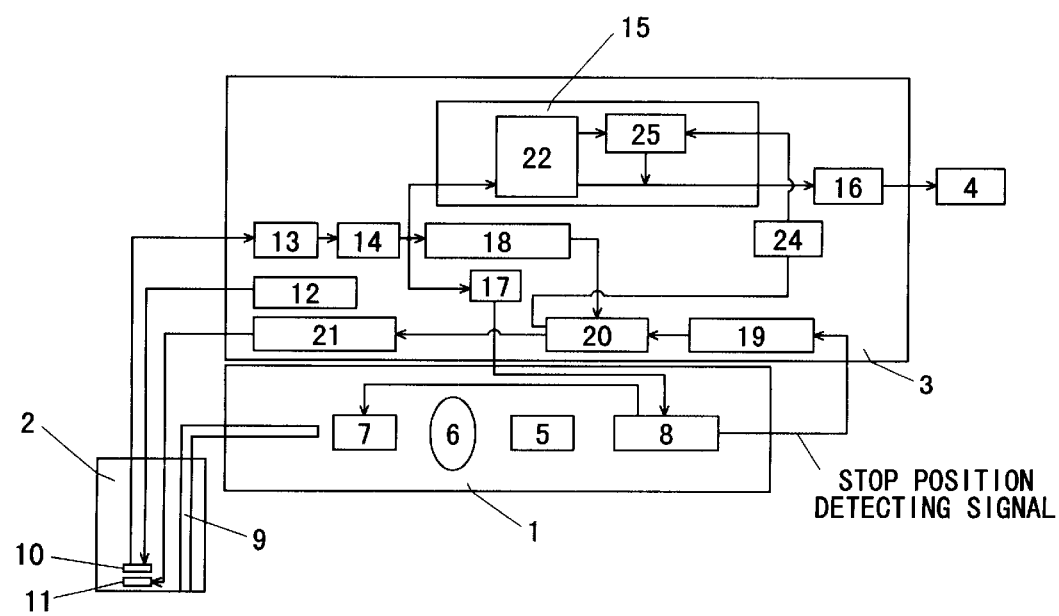
FIG. 12 is a block diagram showing the entire configuration of the endoscope system according to the ninth embodiment of the present invention.

FIG. 12 is an entire configuration diagram of an endoscope system according to the ninth embodiment of the present invention. This embodiment differs from the control system shown in FIG. 3 in that the drive circuit 21 is specified to be a liquid-crystal drive circuit, in that the image magnifying circuit 26 is replaced by an optical information display circuit 25, and in that an optical information calculating circuit 24 intervenes between the lens control circuit 20 and the optical information display circuit 25. However, since flow of the image information substantially is the same as the first embodiment explained in reference to FIG. 3, a detailed explanation is omitted. According to this embodiment, in response to the decision by the lens control circuit 20, which of the near observation mode and the normal observation mode is selected is determined, and the result is fed back to the optical information calculating circuit 24, which performs calculation processing regarding various information including the optical information such as the depth of field and the optical system magnification. The result of the calculation is fed back to the optical information display circuit 25, which, in accordance with this signal, processes an image signal selected by the image generating circuit 22 so that the optical information in the near mode and the magnifying mode are displayed on the display unit 4. For example, in the case of the optical system of the first embodiment, the displayed information may be shown as:

| | | |
|---|---|---|
| Near mode: | Range of View | 7.15 mm–40.4 mm |
| Far mode: | Range of View | 1.84 mm–2.70 mm (Mag. x0.405-) |

Configuration may be made so that selection of the image information to be displayed on the screen is made extraneously or so that calculation of optical information is revised upon determination of the type of the endoscope currently connected with the processor in accordance with given peculiar information on the endoscope not shown.

Figure 13A:
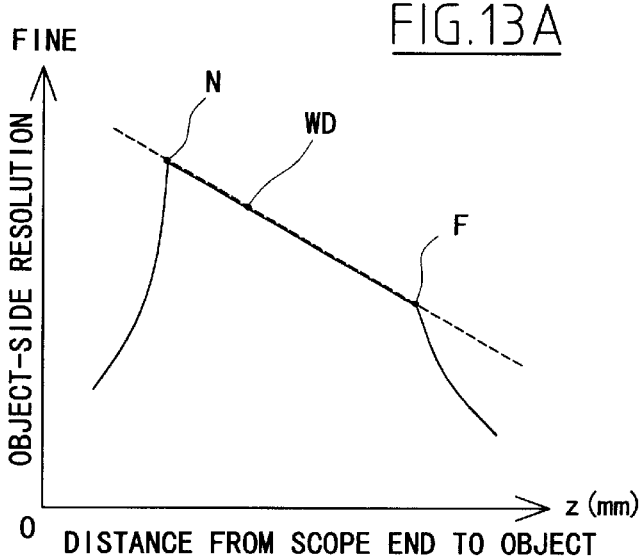
FIGS. 13A–13C are explanatory views which schematically show the relationship between the distance from the endoscope end to the object and the diffraction limit.
Figure 13B:
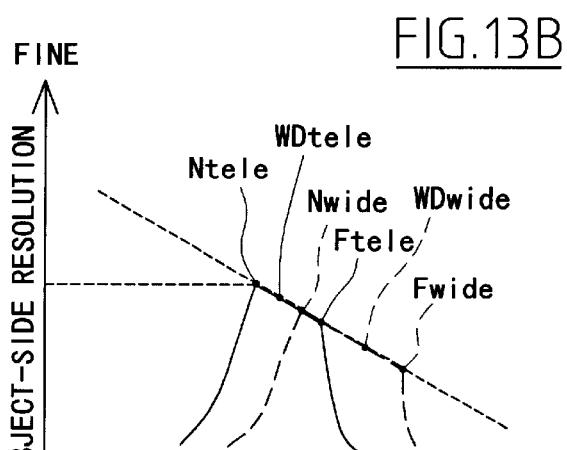
Figure 13C:
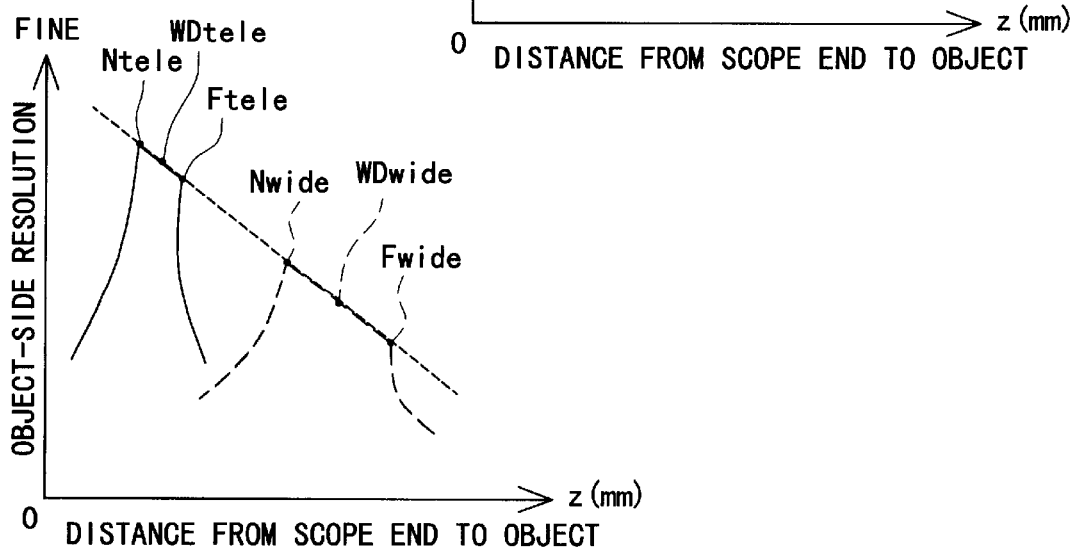

Now, further explanation is made regarding setting of the depth of field in the magnifying observation mode and the normal observation mode according to the above-described embodiments. FIGS. 13A–13C schematically show the relationship between the distance z from the endoscope distal end to the object and the limit of resolution at the distance z.

In general, if correction of aberrations is normalized in the situation where the distance z from the endoscope distal end to the object coincides with the working distance WD, the best system resolution at the working distance WD is determined not by the resolution of the optical system but by the resolution of the CCD in use. On the other hand, if the position of the CCD is fixed while the distance z to the object is varied, the diameter of the spot diagram is changed because of defocusing. Therefore, in the defocused condition, if the resolution of the CCD is less fine than the spot diameter caused by defocusing, the system resolution is determined by the resolution of the CCD and thus the system resolution varies rectilinearly in accordance with magnification change of the optical system. However, if the spot diameter caused by defocusing exceeds the resolution of the CCD, the system resolution is determined by the spot diameter, and thus the resolution is degraded by defocusing. Here, the range where the resolution rectilinearly varies is defined as the depth of field.

Regarding an endoscope optical system having such a characteristic, magnifying observation as performed in the present invention will be discussed. Specifically, discussion is made on the subject regarding how the depth of field in the normal observation mode and the depth of field in the magnifying observation mode are set.

For example, in Japanese Patent Application Preliminary Publication (KOKAI) No. 8-136832, the depth of field varies to satisfy the following conditions:

$$WD_{tele} < WD_{wide} \tag{19}$$

$$N_{tele} < N_{wide} < F_{tele} < F_{wide} \tag{20}$$

where, in reference to the distal end position of the endoscope, $WD_{tele}$ is the best object position (working distance) in the near observation mode, $WD_{wide}$ is the best object position in the normal observation mode, $N_{tele}$ is the near end position of the depth of field in the magnifying observation mode, $N_{wide}$ is the near end position of the depth of field in the normal observation mode, $F_{tele}$ is the far end position of the depth of field in the magnifying observation mode, and $F_{wide}$ is the far end position of the depth of field in the normal observation mode.

Such a configuration is seemingly preferable because the depth of field varies continuously. However, the condition $N_{wide} < F_{tele}$ prevents the value of $N_{tele}$ to be sufficiently small and accordingly the magnification is rendered low. Furthermore, if the focusing control as described in reference to FIG. 3 is made, whichever of the normal observation mode and the near observation mode is selected is indefinite in the region $F_{tele}$–$N_{wide}$ where the depths of field overlap, and thus hunting occurs, which is unfavorable.

Therefore, it is necessary to appropriately set the depth of field in consideration of these problems.

To solve this problem, it is necessary to make configuration so that the following conditions are satisfied, as shown in FIG. 13A:

$$WD_{tele} < WD_{wide} \tag{21}$$

$$N_{tele} < F_{tele} < N_{wide} < F_{wide} \tag{22}$$

If the working distance is designed so, the magnification at $N_{tele}$ can be set high. Furthermore, if the focusing control as described in reference to FIG. 3 is made, a focus evaluation value is calculated out easily, and thus behavior such as hunting would not occur. Also, Condition (22) seemingly shows that the system resolution in the intermediate situation is low. However, since this resolution is a limit resolution, the endoscope may be used for viewing the rough outline of lesion for orientation purpose in the intermediate situation also.

Figure 14A:
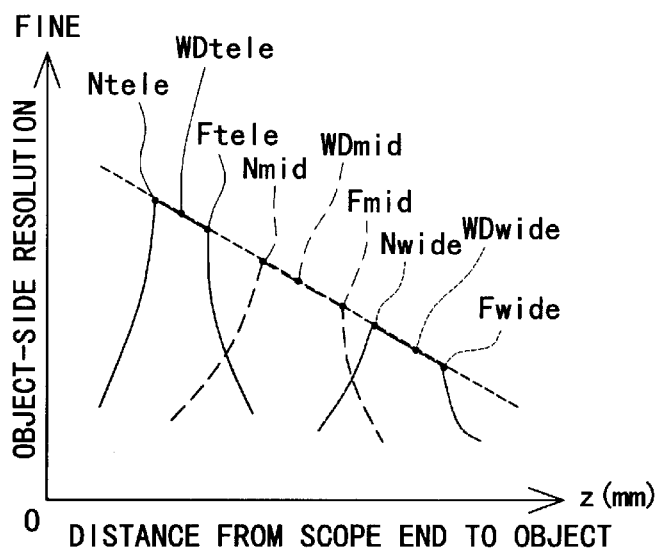
FIGS. 14A–14B are explanatory views which schematically show the relationship between the distance from the endoscope end to the object and the diffraction limit.
Figure 14B:
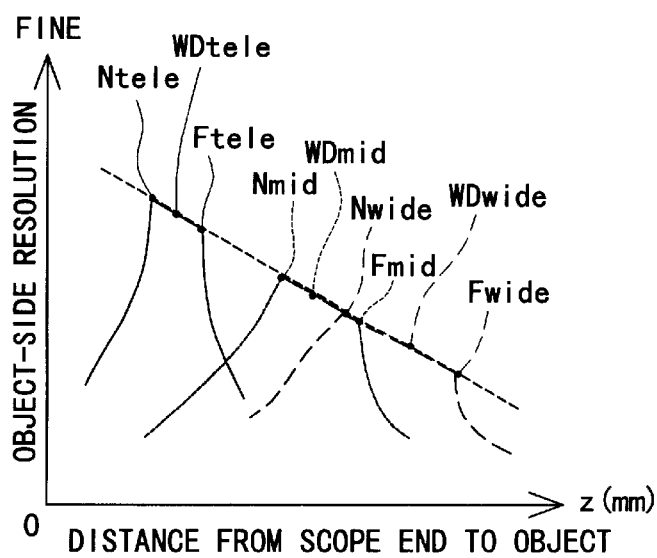
Figure 16:
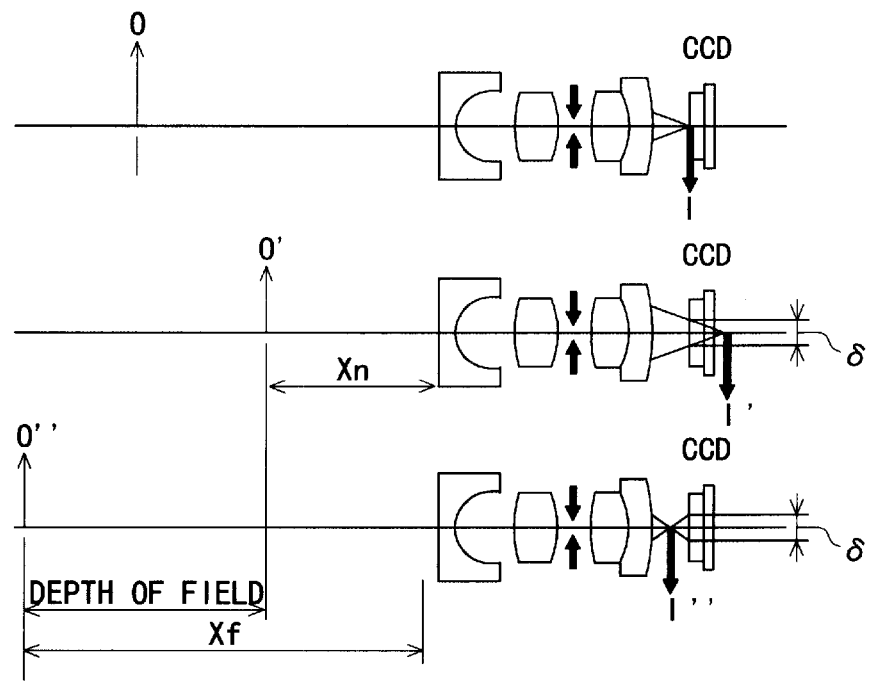
FIG. 16 is a sectional view taken along the optical axis to show the configuration of an endoscope optical system which uses a solid-state image sensor.
Figure 17:
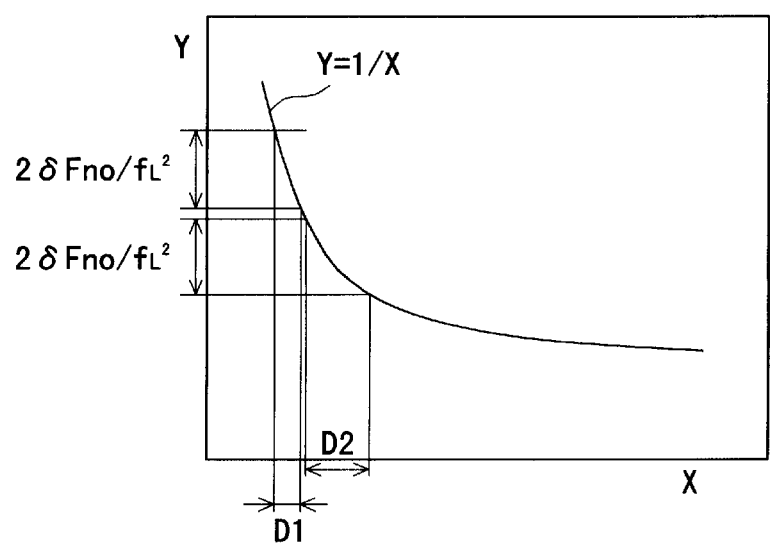
FIG. 17 is a graph to show the relationship between the distance to the object and the depth of field.

However, if a CCD with a large number of pixels is used and values of $N_{wide}$–$F_{wide}$ and $N_{tele}$–$F_{tele}$ are extremely small, it is necessary to set a range in which the in-focus condition is assured in the intermediate situation. In this case, three focusing ranges are set so as to remove the intermediate situation as much as possible in consideration of the restriction regarding the focus control device shown in FIG. 3. In this case, it is preferred to additionally consider the followings. To be specific, as shown in FIG. 14A, arrangement is made to satisfy the following conditions:

$$WD_{tele} < WD_{mid} < WD_{wide} \quad (23)$$

$$F_{tele} < N_{mid} < F_{mid} < N_{wide} \quad (24)$$

where the depth of field is in the range from $N_{mid}$ to $F_{mid}$ under the condition where the working distance in an intermediate observation mode is $WD_{mid}$. According to this arrangement, if an image is in focus in a certain focusing mode, the image is out of focus in the remaining focusing modes. Therefore, it is easy to make judgment at the focus evaluation calculating circuit 18 and thus hunting or the like would not occur. Furthermore, sufficiently high magnification can be achieved because the value of $N_{tele}$ is allowed to be set near.

Alternatively, arrangement may be made to satisfy the following conditions:

$$WD_{tele} < WD_{mid} < WD_{wide} \quad (25)$$

$$F_{tele} < N_{mid} < N_{wide} < F_{mid} \quad (26)$$

where the depth of field is in the range from $N_{mid}$ to $F_{mid}$ under the condition where the working distance in an intermediate observation mode is $WD_{mid}$. This arrangement is effective in the case where the intermediate mode and the far observation mode are frequently used. This arrangement requires an additional mechanism for avoiding problems such as hunting and thus is not preferable in view of cost. However, it is particularly effective in the case where use of a CCD with a multitude of pixels renders the depth of field extremely narrow and thus a depth of field as wide as the conventional endoscope has to be secured by two modes including the intermediate mode and the far observation mode.

The reference example and the first to ninth embodiments are described above, and the optical data are shown regarding the first to seventh embodiments. In particular, values of the above-mentioned numerical conditions are listed in a table shown in FIG. 15.

One of the characteristics of the above-described reference example and the embodiments is to design WD in the near mode to be short so as to provide as high a magnification as possible. For example, according to the reference example, the ratio of the working distance to the focal length in the near observation mode is:

$$WD_{tele}/f_{tele} = 0.74$$

However, this arrangement is unfavorable in that too long a focal length in the near observation mode in reference to the working distance in the near observation mode renders the depth of field narrow, as described above, and thus causes poor operability.

To conclude, if the present invention as described above is specified in view of another aspect, it is important to limit the ratio to the focal length in the near observation mode in an appropriate conditional range.

In consideration of the sixth embodiment, it is preferred that the upper limit value of the ratio is set to be:

$$WD_{tele}/f_{tele} = 1.86$$

If this value is exceeded, $WD_{tele}$ becomes too small and accordingly raises another problem that the object critically fails to receive illumination light.

In practice, the upper limit value is allowed to be:

$$WD_{tele}/f_{tele} = 1.13$$

as in the fifth embodiment.

In each of the embodiments, we have supposed that the resolution of the CCD corresponds to a space for three (=K: K is the coefficient of the allowable circle of confusion) pixels arranged at 3 $\mu$m pitch in calculating the depth of field. Here, if the aperture is stopped too narrow, the resolution of the optical system is uniquely determined in terms of wave optics rather than by aberration performance. Therefore, according to this embodiment, it is desirable that $F_{no}$, which varies in accordance with focus adjustment, assumes a value smaller than the critical value which influences the resolution in terms of wave optics.

A value of $F_{no}$ that becomes the diffraction limit not exceeding the resolution of the CCD is given by:

$$F_{no} 3 \times 3\ \mu m/(1.22 \times 546.07\ nm) = 13.5$$

It is necessary that $F_{no}$ is equal to or smaller than this value. It is noted that 546.07 nm is a wavelength of e-line rays. As obviously known by the table of FIG. 15, each embodiment sufficiently satisfies this condition regarding the diffraction limit irrespective of variation of $F_{no}$ caused by focus adjustment.

What is claimed is:

1. An endoscope system which is adjustable to a plurality of object distances and which is provided with a photographing optical system to display an image for magnifying observation, comprising:

an optical system which allows switching between a normal observation image and a near observation image by operation of a focus adjustment device for changing a focal length and a working distance;

a solid-state image sensor which photographs an image formed by said optical system;

an image display unit which displays the image;

an image control device which generates an image to be displayed on said image display unit on the basis of information from said solid-state image sensor and which controls switching between image processing modes;

a calculating device which calculates optical amounts representing a situation of said optical system; and an optical system control device which controls said optical system;

wherein in operation of said focus adjustment device, the following conditions are satisfied:

$$WD_{wide} > WD_{tele}$$

$$f_{wide} \geq f_{tele}$$

$$N_{tele} < F_{tele} < N_{wide} < F_{wide}$$

where $f_{wide}$ is a focal length in a normal observation mode, $WD_{wide}$ is a working distance in the normal observation mode, $N_{wide}$, $F_{wide}$ are a near end position and a far end position, respectively, of a depth of field in the normal observation mode in reference to an endoscope distal end position, $f_{tele}$ is a focal length in a near observation mode, $WD_{tele}$ is a working distance in the near observation mode, and $N_{tele}$, $F_{tele}$ are a near end position and a far end position, respectively, of a depth of field in the near observation mode in reference to the endoscope distal end position, wherein said image control device controls a ratio of an amount of information $\alpha$ possibly appearing on said solid-state image sensor to an amount of image information β displayed on said image display unit in the near observation mode to be $\alpha/\beta \geq 1$, wherein said image control device performs switching of the image processing modes in accordance with the situation of said optical system on the basis of a signal which is generated by said optical system control device and which is supplied to said focus adjustment device, and wherein said image control device performs processing such that a calculation result of the optical amounts, which is obtained by said calculating device on the basis of the signal supplied to said focus adjustment device and which represents the situation of said optical system, is displayed on said display unit.

2. An endoscope system in which a normal observation image and a near observation image are photographed by a solid-state image sensor upon operation of a focus adjustment device for changing a focal length and a working distance, wherein the following conditions are satisfied:

$$WD_{wide} > WD_{tele}$$

$$f_{wide} \geq f_{tele}$$

where $f_{wide}$ is a focal length in a normal observation mode, $WD_{wide}$ is a working distance in the normal observation mode, $f_{tele}$ is a focal length in a near observation mode, and $WD_{tele}$ is a working distance in the near observation mode.

3. An endoscope system according to claim 2, further comprising a light adjustment device for maintaining a constant brightness of an image on said display unit, which image varies in accordance with change of the working distance associated with operation of said focus adjustment device.

4. An endoscope system in which a normal observation image and a near observation image are photographed by a solid-state image sensor upon operation of a focus adjustment device for changing a focal length and a working distance, wherein the following conditions are satisfied:

$$WD_{wide} > WD_{tele}$$

$$f_{wide} \geq 1.1 \cdot f_{tele}$$

$$P_{exp} < 0$$

where $f_{wide}$ is a focal length in a normal observation mode, $WD_{wide}$ is a working distance in the normal observation mode, $f_{tele}$ is a focal length in a near observation mode, $WD_{tele}$ is a working distance in the near observation mode, and $P_{exp}$ is an exit pupil position of said optical system in reference to a position of said solid-state image sensor.

5. An endoscope system according to claim 2 or 4, wherein the following condition is satisfied:

$$N_{tele} < F_{tele} < N_{wide} < F_{wide}$$

where $N_{wide}$, $F_{wide}$ are a near end position and a far end position, respectively, of a depth of field in the normal observation mode in reference to an endoscope distal end position, and $N_{tele}$, $F_{tele}$ are a near end position and a far end position, respectively, of a depth of field in the near observation mode in reference to the endoscope distal end position.

6. An endoscope system according to claim 5, further satisfying the following conditions:

$$WD_{tele} < WD_{mid} < WD_{wide}$$

$$F_{tele} < N_{mid} < F_{mid} < N_{wide}$$

where $WD_{mid}$ is a working distance in an intermediate observation mode, and $N_{mid}$, $F_{mid}$ are a near end position and a far end position, respectively, of a depth of field in the intermediate observation mode, in reference to the endoscope distal end position.

7. An endoscope system according to claim 6, further comprising a control device that supplies a control signal to said focus adjustment device on the basis of a signal from said solid-state image sensor, wherein switching control of image processing modes in accordance with a situation of the optical system is performed on the basis of said control signal.

8. An endoscope system according to claim 5, further satisfying the following conditions:

$$WD_{tele} < WD_{mid} < WD_{wide}$$

$$F_{tele} < N_{mid} < N_{wide} < F_{mid}$$

where $WD_{mid}$ is a working distance in an intermediate observation mode, and $N_{mid}$, $F_{mid}$ are a near end position and a far end position, respectively, of a depth of field in the intermediate observation mode, in reference to the endoscope distal end position.

9. An endoscope system according to claim 8, further comprising a control device that supplies a control signal to said focus adjustment device on the basis of a signal from said solid-state image sensor, wherein switching control of image processing modes in accordance with a situation of the optical system is performed on the basis of said control signal.

10. An endoscope system according to claim 2 or 4, wherein the following condition is satisfied:

$$N_{tele} < N_{wide} < F_{tele} < F_{wide}$$

where $N_{wide}$, $F_{wide}$ are a near end position and a far end position, respectively, of a depth of field in the normal observation mode in reference to an endoscope distal end position, and $N_{tele}$, $F_{tele}$ are a near end position and a far end position, respectively, of a depth of field in the near observation mode in reference to the endoscope distal end position.

11. An endoscope system according to claim 2, 3 or 4, further comprising a control device that sets, at least in the near observation mode, a ratio of an amount of possible image information α appearing on said solid-state image sensor to an amount of image information β displayed on said display unit to be $\alpha/\beta \geq 1$.

12. An endoscope system according to claim 11, wherein said calculating device performs re-calculation upon a value of $\alpha/\beta$ which is set by said image control device as calculating the optical amounts being fed back.

13. An endoscope system according to claim 11, wherein said control device is configured to prevent degraded video on a marginal portion of the image in the near observation mode to be displayed.

14. An endoscope system according to claim 13, wherein a center position w1 of the image information displayed on said image display unit corresponds to a point existing in a central area 25% of the possible image information on said solid-state image sensor.

15. An endoscope system according to claim 11, wherein a center position w1 of the image information displayed on said image display unit corresponds to a point existing in a central area 25% of the possible image information on said solid-state image sensor.

16. An endoscope system according to claim 2, 3 or 4, further satisfying the following condition:

$$0.74 < WD_{tele}/f_{tele} < 1.86$$

so that the working distance in the near observation mode is sufficiently short in reference to the focal length of the optical system, to obtain a sufficiently high magnification.

17. An endoscope system according to claim 2, 3 or 4, further satisfying the following condition:

$$0.74 < WD_{tele}/f_{tele} < 1.13$$

so that the working distance in the near observation mode is sufficiently short in reference to the focal length of the optical system, to obtain a sufficiently high magnification.

18. An endoscope system according to claim 2, 3 or 4, wherein an effective aperture diameter ratio $F_{no}$ is variable in such a range that a value in said range is equal to or smaller than a diffraction limit.

19. An endoscope system according to claim 18, wherein the following condition is satisfied:

$$F_{no} < K \cdot P_x/(1.22 \times 546.07 \times 10^{-6})$$

where K is a coefficient of a permissible circle of confusion.

* * * * *